US012767927B2

(12) United States Patent
Pasca et al.

(10) Patent No.: US 12,767,927 B2
(45) Date of Patent: Oct. 20, 2026

(54) HUMAN CELLULAR MODEL FOR INVESTIGATING CORTICO-STRIATAL-MIDBRAIN NEURAL PATHWAYS

(71) Applicant: The Board of Trustees of the Leland Stanford Junior University, Stanford, CA (US)

(72) Inventors: Sergiu P. Pasca, Menlo Park, CA (US); Yuki Miura, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1115 days.

(21) Appl. No.: 17/773,429

(22) PCT Filed: Oct. 29, 2020

(86) PCT No.: PCT/US2020/058009
§ 371 (c)(1),
(2) Date: Apr. 29, 2022

(87) PCT Pub. No.: WO2021/087145
PCT Pub. Date: May 6, 2021

(65) Prior Publication Data

US 2022/0364053 A1 Nov. 17, 2022

Related U.S. Application Data

(60) Provisional application No. 62/928,905, filed on Oct. 31, 2019.

(51) Int. Cl.
*C12N 5/0793* (2010.01)

(52) U.S. Cl.
CPC ........ *C12N 5/0619* (2013.01); *C12N 2501/13* (2013.01); *C12N 2501/415* (2013.01); *C12N 2506/45* (2013.01)

(58) Field of Classification Search
CPC .............. C12N 5/0619; C12N 2501/13; C12N 2501/415; C12N 2506/45
See application file for complete search history.

(56) References Cited

U.S. PATENT DOCUMENTS

| | | | | |
|---|---|---|---|---|
| 10,323,229 | B1 | 6/2019 | Li | |
| 2018/0021383 | A1 | 1/2018 | George et al. | |
| 2018/0282689 | A1 | 10/2018 | Andersen et al. | |
| 2018/0298330 | A1 | 10/2018 | Bolognin et al. | |
| 2018/0334646 | A1* | 11/2018 | Song | C12M 21/08 |

FOREIGN PATENT DOCUMENTS

| | | | | |
|---|---|---|---|---|
| WO | WO-2019023693 A1 * | 1/2019 | | A61K 35/545 |

OTHER PUBLICATIONS

Crawford TQ, Roelink H. The notch response inhibitor DAPT enhances neuronal differentiation in embryonic stem cell-derived embryoid bodies independently of sonic hedgehog signaling. Dev Dyn. Mar. 2007;236(3):886-92. doi: 10.1002/dvdy.21083 (Year: 2007).*

Rashid MA, Katakura M, Kharebava G, Kevala K, Kim HY. N-Docosahexaenoylethanolamine is a potent neurogenic factor for neural stem cell differentiation. J Neurochem. Jun. 2013;125(6):869-84. doi: 10.1111/jnc.12255. Epub May 13, 2013. (Year: 2013).*

Pasca, S.P. Building three-dimensional human brain organoids. Nat Neurosci. Mar. 28, 2018. https://doi.org/10.1038/s41593-018-0107-3 (Year: 2018).*

Pasca (Jan. 25, 2018) et al. "The rise of three-dimensional human brain cultures". Nature, vol. 553, No. 7689, pp. 437-445.

Arber et al. (2015) "Activin A directs striatal projection neuron differentiation of human pluripotent stem cells," Development, vol. 142, pp. 1375-1386.

Carr et al. (2013) "Developmentally coordinated extrinsic signals drive human pluripotent stem cell differentiation toward authentic DARPP-32+ medium-sized spiny neurons," Development, vol. 140. pp. 301-312.

Ma et al. "Human embryonic stem cell-derived GABA neurons correct locomotion deficits in quinolinic acid-lesioned mice," Cell Stem Cell, Mar. 15, 2012 (Mar. 15, 2012), vol. 10, pp. 455-464.

Pasca et al. (2019) "Assembling human brain organoids," Science, vol. 1-4, pp. 126-127.

Carri et al.(2013) "Developmentally coordinated extrinsic signals drive human pluripotent stem cell differentiation toward authentic DARPP-32+ medium-sized spiny neurons." *Development*, 140(2), p. 301-312.

Jo et al. (2016) "Midbrain-like organoids from human pluripotent stem cells contain functional dopaminergic and neuromelanin-producing neurons." *Cell stem cell*, 19(2), 248-257.

Birey et al. (2017) Assembly of functionally integrated human forebrain spheroids. *Nature*, 545(7652), p. 54-59.

Yan et al. (2018). "Derivation of cortical spheroids from human induced pluripotent stem cells in a suspension bioreactor." *Tissue Engineering Part A*, 24(5-6), p. 418-431.

Yoon et al. (2019) "Reliability of human cortical organoid generation." *Nature methods*, 16(1), p. 75-78.

Tanaka et al. (2021) "Regional specification and complementation with non-neuroectodermal cells in human brain organoids." *Journal of Molecular Medicine*, 99(4), p. 489-500.

Miura et al. (2020) "Generation of human striatal organoids and cortico-striatal assembloids from human pluripotent stem cells." *Nature Biotechnology*, 38(12), p. 1421-1430.

Wu et al. (2018) "A chemical recipe for generation of clinical-grade striatal neurons from hESCs." *Stem Cell Reports*, 11(3), p. 635-650.

* cited by examiner

*Primary Examiner* — Peter Paras, Jr.
*Assistant Examiner* — Gillian C. Reglas
(74) *Attorney, Agent, or Firm* — Andrew R. Guzman; Pamela J. Sherwood; Bozicevic, Field & Francis LLP

(57) ABSTRACT

Human striatal and midbrain organoids or spheroids are generated in vitro, which may be generated at least in part from human pluripotent stem (hPS) cells. Such spheroids model the regions of the human brain and comprise specific sets of cells that are associated with the striatum, including mature medium spiny neurons, and midbrain of a human, and that can be subsequently assembled with the cortex to form cortico-striatal-midbrain circuits in vitro.

5 Claims, 6 Drawing Sheets

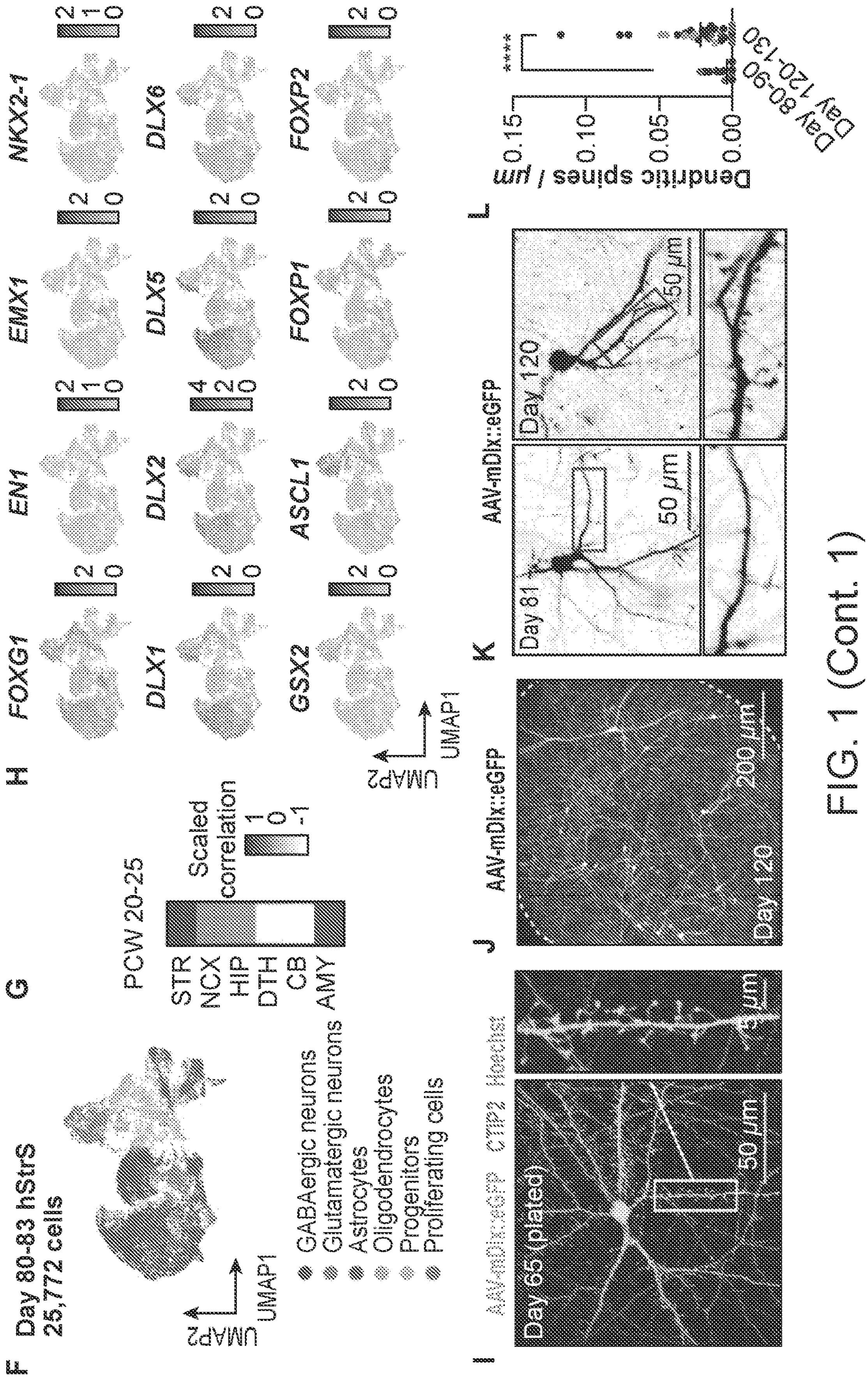
FIG. 1 (Cont. 1)

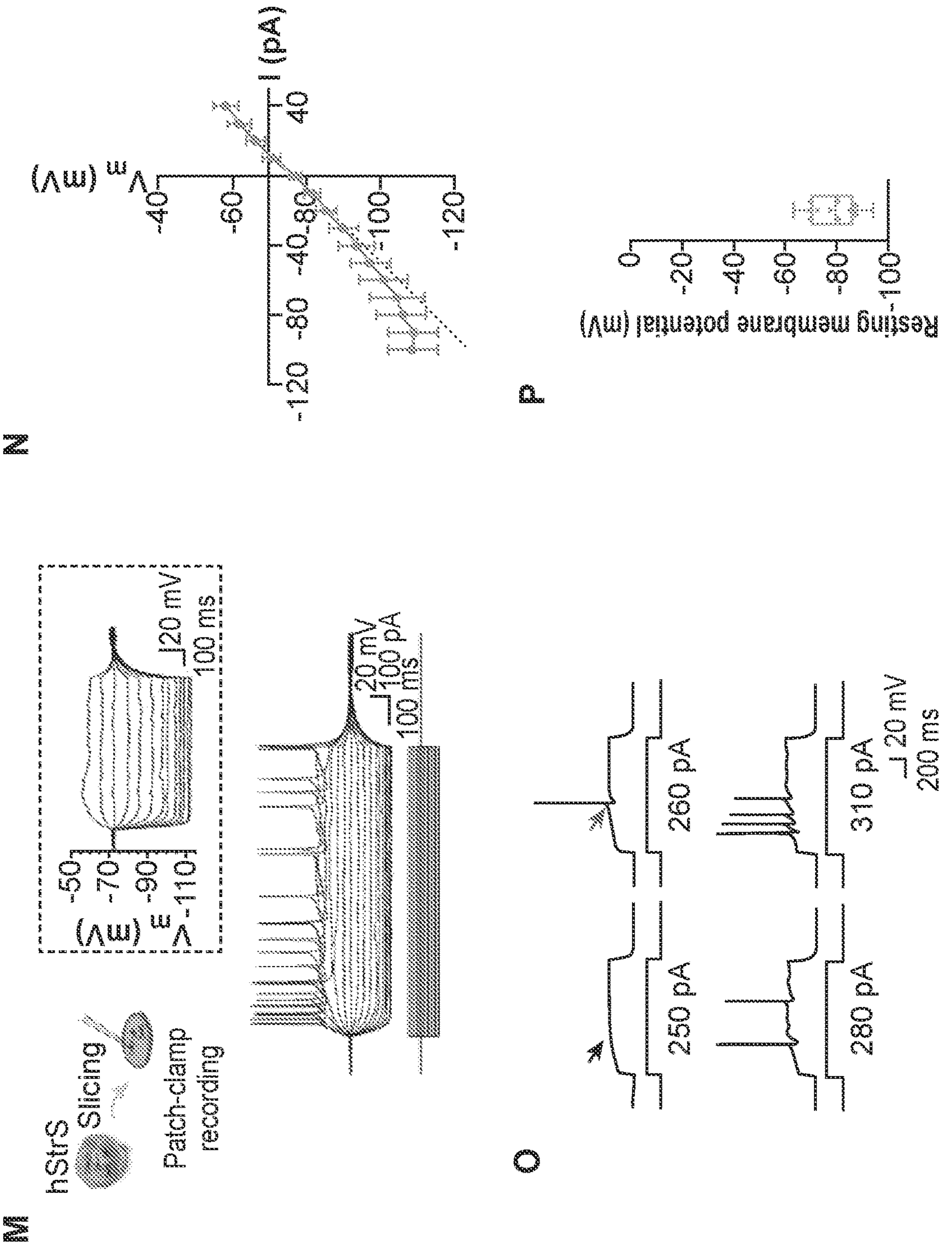
FIG. 1 (Cont. 2)

HUMAN CELLULAR MODEL FOR INVESTIGATING CORTICO-STRIATAL-MIDBRAIN NEURAL PATHWAYS

CROSS REFERENCE TO RELATED APPLICATIONS

This application claims priority to U.S. Provisional Application No. 62/928,905, filed Oct. 31, 2019, which is incorporated herein in its entirety for all purpose.

GOVERNMENT RIGHTS

This invention was made with Government support under contract MH107800 awarded by the National Institutes of Health. The Government has certain rights in the invention.

BACKGROUND OF THE INVENTION

Neural projections from pyramidal neurons in the cerebral cortex towards the striatum are essential components of the neural circuits controlling motivated behavior. This connectivity between the cerebral cortex and the striatum is unidirectional with pyramidal cortical neurons projecting into striatum, and then medium spiny neurons in the striatum subsequently connecting to midbrain dopaminergic neurons as part of the direct and indirect basal ganglia pathways. Dysfunction in this cortico-striatal pathway is thought to contribute to severe neuropsychiatric disorders such as schizophrenia, obsessive-compulsive disorder, Tourette syndrome, Huntington's disease and autism spectrum disorder (ASD) (Shepherd and Gordon, 2013).

However, the specific molecular and cellular mechanisms leading to disease in these patients are still not fully understood mostly due to the inaccessibility to direct investigation of these pathways in the intact, functional human brain and challenges with translating findings from animal models.

Therefore, there is urgent need to develop human cellular models that realistically capture neural circuits formation, function and dysfunction (Pasca, 2018).

SUMMARY OF THE INVENTION

Compositions and methods are provided for in vitro generation of human striatal organoids or spheroids (hStrS) and human midbrain organoids or spheroids (hMbS), which may be generated entirely from human pluripotent stem (hPS) cells. Such spheroids, which may also be referred to as brain region-specific or regionalized organoids, represent the human striatum (basal ganglia) and human midbrain (including substantia nigra) and contain specific sets of cells (e.g. neurons, glial cells) that are associated with the cortex, striatum (basal ganglia) and midbrain of a human.

The hStrS can be functionally integrated with human cerebral cortical spheroids (hCS), which include human cortical neurons such as glutamatergic pyramidal neurons, to provide a cortico-striatal assembloids (hCS-hStrS). Functionally integrated cells interact in a physiologically relevant manner, e.g. forming synapses, releasing neurotransmitters. Human cortical neurons in the hCS-hStrS project from the hCS to the hStrS forming functional cortico-striatal neural circuits. Using a combination of viral tracing and live imaging, evidence is provided herein for the formation of an in vitro generated human cortico-striatal neural circuit, which provides useful modeling of cortico-striatal pathway development and dysfunction.

The hStrS can also be functionally integrated with hMbS to provide a midbrain-striatal assembloid (hMbS-hStrS). Human midbrain neurons, e.g. dopaminergic neurons, project from the midbrain into the hStrS forming striato-midbrain neural circuits. Dopaminergic inputs from the midbrain to the striatum (basal ganglia) are thought to play a crucial role in the development and maturation of the striatum and therefore these assembloids provide unique opportunities to study development and dysfunction of the striatum. Striatal neurons in hStrS also project into the hMbS to provide GABAergic modulation of midbrain dopaminergic neurons. Furthermore, hMbS can be combined with the hCS and hStrS to form assembloids containing cortico-striatal and striato-midbrain neural circuits, therefore allowing for the concurrent study of glutamatergic and dopaminergic input into the striatum (basal ganglia).

The assembloids, i.e. hCS-hStrS, hMbS-hStrS and assembloids comprising hCS, hStrS and hMbS, provide unique opportunities for analysis of the development and function of neural circuits between the human cerebral cortex, striatum and midbrain. Furthermore, these assembloids provide a model to study how specific neurologic or psychiatric disorders impair these neural circuits. Of particular relevance are those neurologic or psychiatric disorders that are associated with cortico-striatal dysfunction, such as schizophrenia, obsessive-compulsive disorder, Tourette syndrome, Parkinson's disease, Huntington's disease and ASD.

In some embodiments, assembloids are provided in which one or more of the cells have been genetically modified to provide for additional functionality in screening. For example, one or more of cortical neurons, striatal neurons and midbrain neurons can be genetically modified to express a fluorescent calcium indicator, which indicators are known and used in the art. One or more of cortical neurons, striatal neurons (medium spiny neurons) and midbrain neurons (dopaminergic neurons) can be genetically modified to express a light activated opsin. In some embodiments, an assembloid comprises neurons expressing an opsin, and other neurons expressing a fluorescent calcium indicator, where a functional relationship between the neurons is demonstrated by using light to activate a neuron, and observing a calcium indicator response from another neuron.

Also provided are spheroids, i.e. hStrS and hMbS, and methods of making said spheroids, as further defined herein. Also provided are assembloids, i.e. hCS-hStrS, hMbS-hStrS and assembloids comprising hCS, hStrS and hMbS, and methods of making said assembloids, as further defined herein.

Also provided are methods for determining the activity of a candidate agent neural circuits in the assembloids, the method comprising contacting the candidate agent with the assembloid. The cells present in the assembloid optionally comprise at least one allele encoding a mutation associated with, or potentially associated with, a neurologic or psychiatric disorder, and determining the effect of the agent on morphological, genetic or functional parameters, including without limitation neuron number, neuron function, gene expression profiling, cell death, single cell gene expression (RNA-seq), calcium imaging with pharmacological screens, patch-clamp recordings, modulation of synaptogenesis, and the like.

These and other objects, advantages, and features of the invention will become apparent to those persons skilled in the art upon reading the details of the subject methods and compositions as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

(FIG. 10) Representative traces showing slow-ramp depolarization of hSyn1::eYFP labeled hStrS neurons at day 160. The black arrow: slow-ramp depolarization, the red arrow: delayed first spike. (FIG. 1P) Resting membrane potential. n=13 cells from hStrS at day 160-170.

(FIG. 2R) Maximum spike frequency. n=17 cells in hStrS, n=25 cells in hCS-hStrS from 3 hiPS cell lines.

(FIG. 3D) Single cell-RNA-sequencing analysis from approximately 2,720 cells dissociated from day 92 hMbS reveals distinct populations of midbrain dopaminergic neurons (mDA), floor plate, Glutamatergic neurons, GABAergic neurons, radial glia and neural progenitor cells. (FIG. 3E) Single cell-RNA-sequencing analysis reveals strong expression of genes enriched in floor plate (SHH, FOXA2) and m DA (TH, NR4A2), as well as glutamatergic (SLC17A7) and GABAergic (SLC32A1) neurons. (FIG. 3F) Representative image of midbrain-striatal assembloids; hMbS infected with AAV-SYN1:eYFP and hStrS infected with AAV-SYN1::mCherry were separately differentiated and placed adjacent to each other inside a conical tube. After 3 days, those spheroids were successfully assembled. (FIG. 3G) Representative image of midbrain-striatal assembloids; hMbS co-infected with AAV-TH::Cre and AAV-DIO-eYFP and hStrS without fluorescence were separately differentiated and placed adjacent to each other inside a conical tube. After 3 days, those spheroids were successfully assembled and started formation of projections from hMbS to hStrS.

Figure 1:
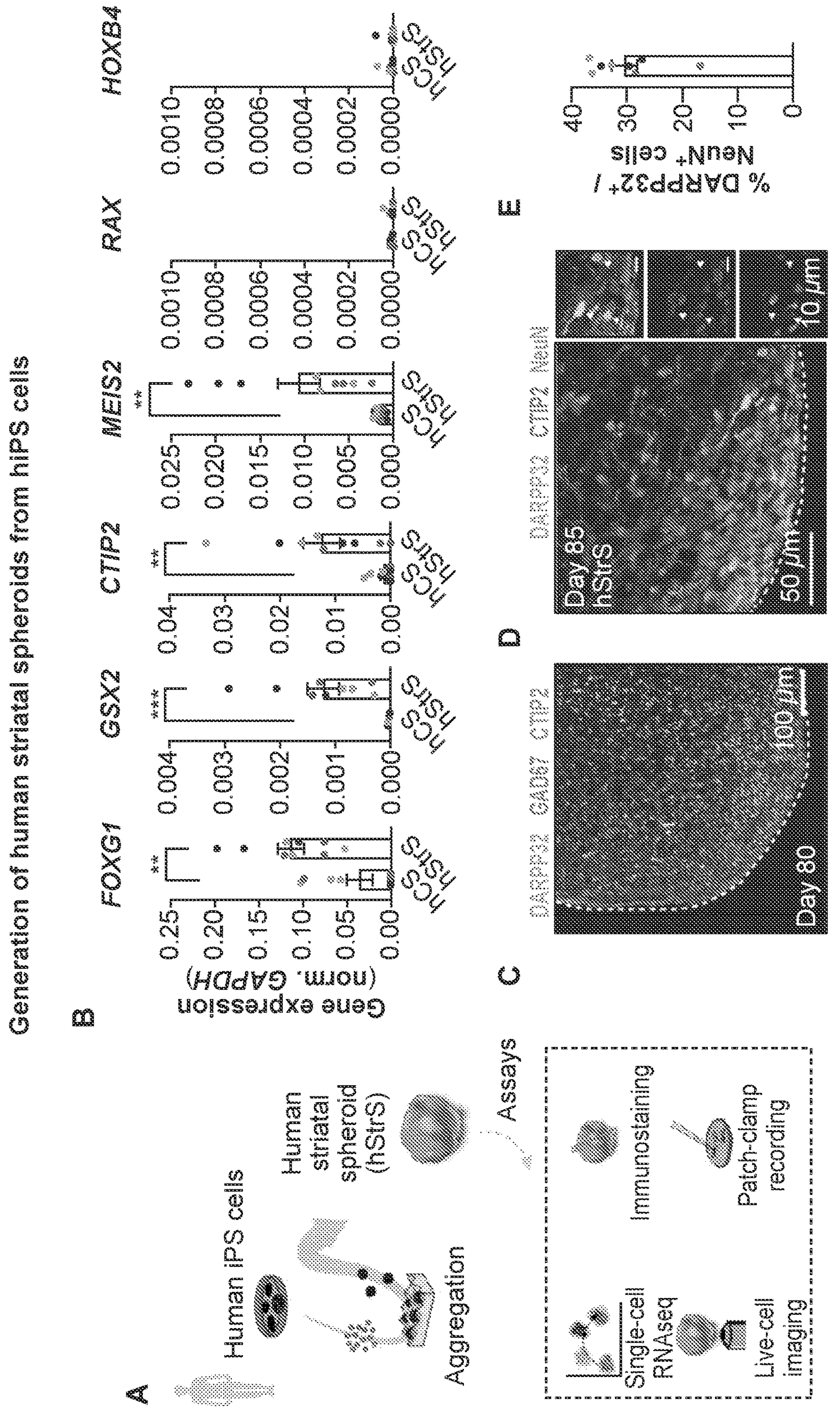
FIG. 1A-1P. Generation of human striatal spheroids (hStrS) from human pluripotent stem cells (FIG. 1A) Scheme illustrating the main stages for the generation of hStrS (also named or basal ganglia organoids) from human induced pluripotent stem (hiPS) cells and subsequent analysis by qPCR, sectioning and immunohistochemistry (IHC), single cell RNA-seq, live cell imaging and electrophysiological recordings (FIG. 1B) Levels of gene expression of forebrain marker FOXG1 and lateral ganglionic eminence (LGE) markers GSXZ CTIP2 and MEIS2 in hStrS and human cortical spheroids (hCS) at day 23. Levels of gene expression were normalized to GADPH. n=9 spheroids produced from 4 hiPS cell lines.
(FIG. 1C) Immunostaining of hCS and hStrS at day 80 showing protein expression of DARPP32, GAD67, CTIP2.
FIG. 1D, E) Immunostaining of hStrS at day 85 showing protein expression of DARPP32, CTIP2 and NeuN and quantification. n=8 spheroids produced from 3 hiPS cell lines. Arrowheads indicate cells expressing DARPP32 and NeuN, indicative of medium spiny neurons.
(FIG. 1F) Single cell-RNA-sequencing analysis from approximately 25,772 cells dissociated from day 80-83 hStrS reveals distinct populations of GABAergic neurons, neural progenitor cells, astrocytes, oligodendrocytes and glutamatergic neurons.
(FIG. 1G) Correlation to the BrainSpan dataset to the human developing brain (PCW 20-25).
(FIG. 1H) Single cell-RNA-sequencing analysis reveals strong expression of genes enriched in forebrain (FOXG1) and LGE (DLX1, DLX2, DLX5, DLX6, GSX2, ASCL1, FOXP1 and FOXP2) but not of genes in medial ganglionic eminence (MGE; NKX2-1) or in cerebral cortex (EMX/).
(FIG. 1I) Representative image of a control hStrS cell transfected with AAV-mDlx::eGFP, showing miColx::eGFP+cells develop dendritic spine-like structures at 65 days (in this case after dissociation and plating in 2D).
(FIG. 1J, K, L) Representative image of hStrS transfected with AAV-mDlx::eGFP showing miColx::eGFP$^{+}$ cells with dendritic spine-like structures in 3D culture at day 81 and 120, and quantification. n=40 neurons from 2 hiPS cell lines in day 80-90, n=38 neurons from 3 hiPS cell lines in day 120-130.
(FIG. 1M) Whole cell patch clamp recording and representative membrane response of hSyn1::eYFP labeled hStrS neurons following intracellular current pulse injection.
(FIG. 1N) Curent-frequency (I-V) curve showing inward rectification in hSyn1::eYFP labeled hStrS neurons. n=17 cells from hStrS at day 110-120).

The invention is best understood from the following detailed description when read in conjunction with the accompanying drawings.

DETAILED DESCRIPTION OF THE INVENTION

Before the present compositions and methods are described, it is to be understood that this invention is not limited to particular compositions and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a reprogramming factor polypeptide" includes a plurality of such polypeptides, and reference to "the induced pluripotent stem cells" includes reference to one or more induced pluripotent stem cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

By "pluripotency" and pluripotent stem cells it is meant that such cells have the ability to differentiate into all types of cells in an organism. The term "induced pluripotent stem cell" encompasses pluripotent cells, that, like embryonic stem (ES) cells, can be cultured over a long period of time while maintaining the ability to differentiate into all types of cells in an organism, but that, unlike ES cells, are derived from differentiated somatic cells, that is, cells that had a narrower, more defined potential and that in the absence of experimental manipulation could not give rise to all types of cells in the organism. hiPS cells have a human ES-like morphology, growing as flat colonies with large nucleo-cytoplasmic ratios, defined borders and prominent nuclei. In addition, hiPS cells express several pluripotency markers known by one of ordinary skill in the art, including but not limited to alkaline phosphatase, SSEA3, SSEA4, Sox2, Oct3/4, Nanog, TRA160, TRA181, TDGF 1, Dnmt3b, FoxD3, GDF3, Cyp26a1, TERT, and zf p42. In addition, the hiPS cells are capable of forming teratomas. In addition, they are capable of forming or contributing to ectoderm, mesoderm, or endoderm tissues in a living organism.

As used herein, "reprogramming factors" refers to one or more, i.e. a cocktail, of biologically active factors that act on a cell to alter transcription, thereby reprogramming a cell to multipotency or to pluripotency. Reprogramming factors may be provided to the cells, e.g. cells from an individual with a family history or genetic make-up of interest for heart disease such as fibroblasts, adipocytes, etc.; individually or as a single composition, that is, as a premixed composition, of reprogramming factors. The factors may be provided at the same molar ratio or at different molar ratios. The factors may be provided once or multiple times in the course of culturing the cells of the subject invention. In some embodiments the reprogramming factor is a transcription factor, including without limitation, Oct3/4; Sox2; Klf4; c-Myc; Nanog; and Lin-28.

Somatic cells are contacted with reprogramming factors, as defined above, in a combination and quantity sufficient to reprogram the cell to pluripotency. Reprogramming factors may be provided to the somatic cells individually or as a single composition, that is, as a premixed composition, of reprogramming factors. In some embodiments the reprogramming factors are provided as a plurality of coding sequences on a vector. The somatic cells may be fibroblasts, adipocytes, stromal cells, and the like, as known in the art. Somatic cells or hiPS cells can be obtained from cell banks, from normal donors, from individuals having a neurologic or psychiatric disease of interest, etc.

Following induction of pluripotency, hiPS cells are cultured according to any convenient method, e.g. on irradiated feeder cells and commercially available medium. The hiPS cells can be dissociated from feeders by digesting with protease, e.g. dispase, preferably at a concentration and for a period of time sufficient to detach intact colonies of pluripotent stem cells from the layer of feeders. The spheroids can also be generated from hiPS cells grown in feeder-free conditions, by dissociation into a single cell suspension and aggregation using various approaches, including centrifugation in plates, etc.

Genes may be introduced into the somatic cells or the hiPS cells derived therefrom for a variety of purposes, e.g. to replace genes having a loss of function mutation, provide marker genes, etc. Alternatively, vectors are introduced that express antisense mRNA, siRNA, ribozymes, etc. thereby blocking expression of an undesired gene. Other methods of gene therapy are the introduction of drug resistance genes to enable normal progenitor cells to have an advantage and be subject to selective pressure, for exam ple the multiple drug resistance gene (MDR), or anti-apoptosis genes, such as BCL-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

Disease-associated or disease-causing genotypes can be generated in healthy hiPS cells through targeted genetic manipulation (CRISPR/CAS9, etc.) or hiPS cells can be derived from individual patients that carry a disease-related genotype or are diagnosed with a disease. Moreover, neural and neuromuscular diseases with less defined or without genetic components can be studied within the model system. A particular advantage of this method is the fact that edited hiPS cell lines share the same genetic background as their corresponding, non-edited hiPS cell lines. This reduces variability associated with line-line differences in genetic background. Conditions of neurodevelopmental, neuropsychiatric and neurological disorders that have strong genetic components or are directly caused by genetic or genomic alterations can be modeled with the systems of the invention.

The methods and compositions described herein are associated with brain-region specific spheroids. Brain-region specific spheroids or organoids are three-dimensional (3D) aggregates of cells that resemble particular regions of the human brain and contain functional neurons that are normally associated with that region of the brain. These spheroids are capable of being maintained in suspension culture for long periods of time, e.g. 2 week, 4 weeks, 1 month, 2 months, 3 months, 4 months, 5 months, 6 months or more, without adhering to a surface, e.g. a surface of a culture dish. By functional neurons, it is intended to mean that the neurons are capable of forming functional synapses with other neurons, either in the same spheroid or in another spheroid. The formation of functional synapses can be revealed using calcium imaging, as described in more details in the Examples. For example, the striatal spheroids described herein comprise striatal neurons, such as medium spiny neurons, and the midbrain spheroids described herein comprise dopaminergic A9/A10 neurons.

The methods and compositions described herein are also associated with assembloids comprising more than one (e.g. two or three or more) of these brain-region specific spheroids. The assembloids described herein resemble multiple regions of the brains and contain functional neural circuits between neurons of one spheroid (representing one region) and another spheroid (representing another region). For example, the cortico-striatal assembloids resemble the cerebral cortex and striatum of the human brain and contain neurons (e.g. human cortical neurons) projecting from the cortical spheroid into the striatal spheroid, where these neurons are able functionally synapse with human striatal neurons (e.g. medium spiny neurons) of the striatal spheroid. Similar to the spheroids, these assembloids are also capable of being maintained for long periods of time without adhering to a surface.

Striatum. The human striatum is a region of the forebrain that is understood to act as an integrative hub for information processing in the brain and in coordinating multiple aspects of voluntary motor control. During development of the nervous system, cells of the striatum arise from the Lateral Ganglionic Eminence (LGE) of the ventral forebrain. The striatum is one of the principal components of the basal ganglia of the forebrain, a group of structures known for facilitating movement and receives inputs from the cerebral cortex, substantia nigra and thalamus. Connectivity between the cortex and striatum is unidirectional with pyramidal cortical neurons projecting into the striatum to synapse with medium spiny neurons, which are estimated to represent around 95% of neurons in the human striatum. GABAergic and cholinergic intemeurons form most of the remaining population of neurons in the striatum. In addition to its widespread cortical connectivity, the striatum has extensive bidirectional connections to the midbrain.

The striatum can be divided into two main regions: the dorsal striatum and the nucleus accumbens. The dorsal striatum is associated with mediating cognition involving motor function. Dopaminergic neurons in the substantia nigra project to the dorsal striatum via the nigrostriatal pathway and regulate voluntary movement as part of the basal ganglia circuitry, where dopamine release modulates cortico-striatal transmission in medium spiny neurons expressing the dopamine receptors. The nucleus accumbens is widely associated with its role in the mesolimbic pathway associated with reward and addiction. Dopamine neurons in the ventral tegmental area of the midbrain project into the nucleus accumbens and when activated results in an increase in dopamine levels.

Medium spiny neurons are inhibitory neurons that are the principle neurons of the striatum. They are GABAergic neurons, so named due to their release of the neurotransmitter gamma-aminobutyric acid (GABA). The medium spiny neurons receive excitatory inputs from glutamatergic neurons from the cortex and is the target of dopaminergic neurons from the midbrain, where dopamine is thought to modulate the glutamatergic input.

The medium spiny neurons can be subdivided into two classes based on their projection patterns, as well as their neuropeptide and receptor expression. Medium spiny neurons that send express dopamine D1 receptors form part of the direct pathway. Medium spiny neurons that express dopamine D2 receptors form part of the indirect pathway. Classically, these two striatal medium spiny neuron populations are thought to have opposing effects on basal ganglia output. Activation of the direct medium spiny neurons has been considered to act as a 'go' signal to initiate behavior, whilst activation of the indirect mediirn spiny neurons serves as a 'brake' to inhibit behavior (Yager et al. 2015).

Pyramidal cortical neurons are neurons that project from the cerebral cortex to the striatum. These neurons are excitatory, glutamatergic neurons.

Dopaminergic neurons are collections of neurons that produce the neurotransmitter dopamine. The neurons mainly originate in two nuclei in the human midbrain—the substantia nigra and the ventral tegmental area.

Disease relevance. Dysfunction in neural pathways from the cortex to the striatum (cortico-striatal pathway), which may also involve neural pathways to/from the midbrain, is thought to contribute to severe neuropsychiatric disorders such as schizophrenia, obsessive-compulsive disorder, Tourette syndrome, Huntington's disease, Parkinson's disease and autism spectrum disorder (ASD) (Shepherd and Gordon, 2013). As well as understanding development, the spheroids and assembloids described herein are is useful to model disorders of the cortico-striatal pathway as well as for testing therapeutics including gene therapy and small molecule drugs.

Schizophrenia. The systems of the present invention provide unique opportunities to study schizophrenia. Schizophrenia is a chronic and severe mental disorder that affects an individual's behavior. The underlying cause of schizophrenia is not known, but the disorder has been associated with abnormal cortical dopamine signaling (Shepherd, 2014).

Obsessive-compulsive disorder(OCD) is a mental disorder in which a person feels the need to perform certain routines repeatedly. Cortico-striatal dysfunction is considered a major factor in OCD pathogenesis and functional imaging has shown increased or otherwise abnormal functional connectivity in the cortico-striatal pathways (Shepherd, 2014). Accordingly, the systems described here provide opportunities to further study OCD and develop potential therapeutic treatments.

Tourette syndrome is a neuropsychiatric movement disorder which is clinically characterized by the presence of vocal and motor tics. Whilst the underlying cause is still unclear, various studies support a hypothesis of a dysfunction in the cortico-striatal networks as a neurobiological substrate of tics. The systems described herein therefore allow for further study of the role of the cortico-striatal networks in Tourette syndrome and support the development of treatments.

Huntington's disease is a neurodegenerative disease characterized by the progressive loss of motor and cognitive function caused by degeneration of selected neuronal populations. Huntington's disease is mainly driven by a genetic defect on chromosome 4 that results in an expanded CAG repeat at the encoding site of huntingtin protein. The neurodegenerative process in Huntington's disease mainly affectsthe cortex and striatum. In the striatum primarily affects the medium spiny neurons that form part of the indirect pathway. The role of these pathways in Huntington's disease and potential therapeutic treatments can be further studied using the systems described herein.

Parkinson's disease is a progressive nervous system disorder that affects movement. It develops when neurons connecting the substantia nigra in the midbrain to the striatum degenerate, resulting in a loss of dopamine signaling. There is also evidence that there is a cortico-striatal aspect to the disease (Shepherd, 2014). Accordingly, the systems described herein provide an opportunity to further study the circuits underlying Parkinson's disease and to develop new treatments.

Autism spectrum disorder (ASD) is a developmental disorder characterized by defects in communication and the presence of repetitive/restricted behaviors, and is associated with defects in the striatal circuits. Various studies of ASD-associated genes have demonstrated cortico-striatal involvement. Mutations in SHANK3, a postsynaptic scaffolding protein expressed in medium spiny neurons, cause the ASD-related 22q13.3 deletion syndrome, also known as Phelan-McDerm id syndrome.

The terms "astrocytic cell," "astrocyte," etc. encompass cells of the astrocyte lineage, i.e. glial progenitor cells, astrocyte precursor cells, and mature astrocytes, which for the purposes of the present invention arise from a non-astrocytic cells (i.e., glial progenitors). Astrocytes can be identified by markers specific for cells of the astrocyte lineage, e.g. GFAP, ALDH1L1, AQP4, EAAT1 and EAAT2, etc. Markers of reactive astrocytes include S100, VIM, LCN2, FG FR3 and the like. Astrocytes may have characteristics of functional astrocytes, that is, they may have the capacity of promoting synaptogenesis in primary neuronal cultures; of accumulating glycogen granules in processes; of phagocytosing synapses; and the like. A "astrocyte precursor" is defined as a cell that is capable of giving rise to progeny that include astrocytes.

Astrocytes are the most numerous and diverse neuroglial cells in the CNS. An archetypal morphological feature of astrocytes is their expression of intermediate filaments, which form the cytoskeleton. The main types of astroglial intermediate filament proteins are glial fibrillary acidic protein (GFAP) and vimentin; expression of GFAP, ALDH1L1 and/or AQP4P are commonly used as a specific marker for the identification of astrocytes.

The terms "oligodendrocyte," "oligodendrocyte progenitor cell," etc. can encompass cells of the oligodendrocyte lineage, i.e. neural progenitor cells that ultimately give rise to oligodendrocytes, oligodendrocyte precursor cells, and mature and myelinating oligodendrocytes, which for the purposes of the present invention arise from a non-oligodendrocyte cell by experimental manipulation. Oligodendrocytes may have functional characteristics, that is, they may have the capacity of myelinating neurons; and the like. An "oligodendrocyte precursor" or "oligodendrocyte progenitor cell" is defined as a cell that is capable of giving rise to progeny that include oligodendrocytes. Oligodendrocytes may be present in the assembloids.

Oligodendrocytes are the myelin-forming cells of the central nervous system. An oligodendrocyte extends many processes which contact and repeatedly envelope stretches of axons. Subsequent condensation of these wrapped layers of oligodendrocyte membrane form the myelin sheath. One axon may contain myelin segments from many different oligodendrocytes.

Calcium sensors. Neural activity causes rapid changes in intracellular free calcium, which can be used to track the activity of neuronal populations. Art-recognized sensors for this purpose include fluorescent proteins that fluoresce in the presence of changes in calcium concentrations. These proteins can be introduced into cells, e.g. iPS cells, by including the coding sequence on a suitable expression vector, e.g. a viral vector, to genetically modify neurons generated by the methods described herein. GCaM Ps are widely used protein calcium sensors, which are comprised of a fluorescent protein, e.g. GFP, the calcium-binding protein calmodulin (CaM), and CaM-interacting M13 peptide, although a variety of other sensors are also available. Many different proteins are available, including, forexample, those described in Zhao et al. (2011) Science 333:1888-1891; Mank et al. (2008) Nat. Methods 5(9):805-11; Akerboom et al. (2012) J. Neurosci. 32(40):13819-40; Chen et al. (2013) Nature 499(7458):295-300; etc.; and as described in U.S. Pat. Nos. 8,629,256, 9,518,980 and 9,488,642 and 9,945,844.

Optogenetics integrates optics and genetic engineering to measure and manipulate neurons. Actuators are genetically-encoded tools for light-activated control of proteins; e.g., opsins and optical switches. Opsins are light-gated ion channels or pumps that absorb light at specific wavelengths. Opsins can be targeted and expressed in specific subsets of neurons, allowing precise spatiotemporal control of these neurons by turning on and off the light source. Channel rhodopsins typically allow the fast depolarization of neurons upon exposure to light through direct stimulation of ion channels. Chlamydomonas reinhardtii Channelrhodopsin-1 (ChR1) is excited by blue light and permits nonspecific cation influx into the cell when stimulated. Examples of ChRs from other species include: CsChR (from Chloromonas subdivisa), CoChR (from Chloromonas oogama), and SdChR (from Scherffelia dubia). Synthetic variants have been created, for example ChR2(H134R), C1V1(t/t), ChIEF; ChETA, VChR1, Chrimson, ChrimsonR, Chronos, PsChR2, CoChR, CsChR, CheRiff, and the like. Alternatively, ChR variants that inhibit neurons have been created and identified, for example GtACR1 and GtACR2 (from the cryptophyte Guillardia theta), and variants such as iChloC, SwiChRca, Phobos, Aurora. Halorhodopsin, known as NpHR (from Natronomonas pharaoni), causes hyperpolarization of the cell when triggered with yellow light, variants include Halo, eNpHR, eNpHR2.0, eNpHR3.0, Jaws. Archaerhodopsin-3 (Arch) from Halorubrum sodomense is also used to inhibit neurons.

The terms “treatment”, “treating”, “treat” and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. “Treatment” as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms “individual,” “subject,” “host,” and “patient,” are used interchangeably herein and refer to any mammalian subject for whom diagnosis, treatment, or therapy is desired, particularly humans.

Methods for Producing Spheroids and Assembloids

Methods are provided for the obtention and use of in vitro cell cultures of spheroids/organoids and assembloids where the spheroids and assembloids are produced from human pluripotent stem cells. In some embodiment the human pluripotent stem cells are induced human pluripotent stem (hiPS) cells. In some embodiments the hiPS cells are derived from somatic cells obtained from neurologically normal individuals. In other embodiments the hiPS cells are derived from somatic cells obtained from an individual comprising at least one allele encoding a mutation associated with a disease, including without limitation the neurologic or psychiatric disorder described above.

Human induced pluripotent stem cells. The neural progenitor spheroids can be differentiated from pluripotent stem cells, including without limitation, human induced pluripotent stem cells, hiPS cells. Initially, hiPS cells can be obtained from any convenient source, or can be generated from somatic cells using art-recognized methods. The hiPS cells are dissociated from feeders into single cells and grown in suspension culture, preferably when dissociated as intact colonies. In certain embodiments the culture are feeder layer free, e.g. when grown on vitronectin coated culture dishes. The culture may further be free on non-human components, i.e. xeno-free. The hiPS cells may be cultured in any medium suitable for the growth and expansion of hiPS cells. For example, the medium may be Essential 8 medium. Suspension growth optionally includes in the culture medium an effective dose of a selective Rho-associated kinase (ROCK) inhibitor for the initial period of culture, for up to about 6 hours, about 12 hours, about 18 hours, about 24 hours, about 36 hours, about 48 hours, (see, for example, Watanabe et al. (2007) Nature Biotechnology 25:681 686). Inhibitors useful for such purpose include, without limitation, Y-27632; Thiazovivin (Cell Res, 2013, 23(10):1187-200; Fasudil (HA-1077) HCl (J Clin Invest, 2014, 124(9):3757-66); GSK429286A (Proc Natl Acad Sci USA, 2014, 111(12): E1140-8); RKI-1447; AT13148; etc. In particular embodiments the ROCK inhibitor Y-27632 is used. Optionally a WNT pathway inhibitor such as XAV-939 is added.

Human Striatal Spheroids (hStrS)

To generate hStrS (also named striatal organoids or basal ganglia organoids), after about 5 days, about 6 days, about 7 days, about 8 days, about 9 days, about 10 days in suspension culture, the floating spheroids are moved to neural medium to differentiate neural progenitors. An exemplary neural medium is a medium comprising neurobasal-medium, B-27 supplement minus vitamin A and a GlutaMAX supplement. The neural medium is supplemented with an inhibitor of the Wnt pathway and a recombinant activin A. IWP-2 is an inhibitor of Wnt processing and secretion with IC50 of 27 nM in a cell-free assay, selective blockage of Porcn-mediated Wnt palmitoylation, does not affect Wnt/β-catenin in general and displays no effect against Wnt-stimulated cellular responses. The inhibitor is added, for example, at a concentration of from about 0.1 μM to about 100 μM and may be from about 1 μM to about 25 μM, depending on the activity of the inhibitor that is selected. Other inhibitors include, without limitation, XAV-939 selectively inhibits Wnt/β-catenin-mediated transcription through tankyrase1/2 inhibition with IC50 of 11 nM/4 nM in cell-free assays; ICG-001 antagonizes Wnt/β-catenin/TCF-mediated transcription and specifically binds to element-binding protein (CBP) with IC50 of 3 μM; IWR-1-endo is a Wnt pathway inhibitor with IC50 of 180 nM in L-cells expressing Wnt3A, induces Axin2 protein levels and promotes β-catenin phosphorylation by stabilizing Axin-scaffolded destruction complexes; Wnt-C59 (C59) is a PORCN inhibitor for Wnt3A-mediated activation of a multimerized TCF-binding site driving luciferase with IC50 of 74 μM in HEK293 cells; LGK-974 is a potent and specific PORCN inhibitor, and inhibits Wnt signaling with IC50 of 0.4 nM in TM3 cells; KY02111 promotes differentiation of hiPS cells to cardiomyocytes by inhibiting Wnt signaling, may act downstream of APC and GSK38; IWP-L6 is a highly potent Porcn inhibitor with EC50 of 0.5 nM; WIKI4 is a novel Tankyrase inhibitor with IC50 of 15 nM for TNKS2, and leads to inhibition of Wnt/beta-catenin signaling; FH535 is a Wnt/β-catenin signaling inhibitor and also a dual PPARy and PPARδ antagonist.

In certain embodiments, the neural medium is supplemented with IWP-2, for example at a concentration from about 1 μM to about 10 μM, about 1 μM to about 5 μM, about 2 μM to about 3 μM, or about 2.5 μM. The recombinant activin A may be recombinant human/murine/rat activin A. In certain embodiments, the neural medium is supplemented with human/murine/rat activin A, for example at a concentration from about 10 μg/ml to about 100 μg/ml, from about 25 μg/ml to about 75 μg/ml, from about 40 μg/ml to about 60 μg/ml, or about 50 μg/ml.

To promote striatal patterning, between about 1 day and 10 days, between about 2 days and 9 days, between about 3 days and 8 days, between about 4 days and 7 days, at about 4 days, at about 5 days, at about 6 days, or at about 7 days, after exposure to the inhibitor of the Wnt pathway and the recombinant activin A, the neural medium is further supplemented with an effective dose of a retinoid X receptor (RXR) agonist. In certain embodiments, the neural medium is supplemented with an effective dose of an RXR agonist about 6 days after exposure to the inhibitor of the Wnt pathway and the recombinant activin A.

An effective dose of the RXR agonists may be included in the neural medium, for example at a concentration from about 10 μM to about 200 μM, from about 50 μM to about 150 μM, or from about 75 μM to about 125 μM, depending on the activity of the inhibitor that is selected. Exemplary agonists, without limitation SR11237, bexarotene, AGN194204, LG100268, 9-cis-retinoic acid, methoprene acid. In certain embodiments the RXR agonist is SR11237, for example added at a concentration from about 10 μM to about 200 μM, from about 50 μM to about 150 μM, from about 75 μM to about 125 μM, or about 100 μM.

As demonstrated in the examples, the combined use of an inhibitor of the Wnt pathway, a recombinant activin A and a RXR agonist results in the formation of striatal spheroids with high levels of markers indicative of the human striatum, e.g. at least 3 weeks after the suspension culture of hiPS cells was induced to a neural fate. For example, the striatal spheroids may have high levels of forebrain markers such as FOXG1, and/or high levels of lateral ganglionic eminence (LGE) markers such as GSX2, MEIS2, CTIP2, but low levels of hypothalamus marker gene RAX and spinal cord marker gene HOXB4. Methods for determining levels of marker genes include qPCR as further described in examples. In some embodiments, the methods disclosed herein further comprise determining whether the striatal spheroids express forebrain and LGE markers. A striatal spheroid having high or low levels of a marker gene may have a significantly higher or lower level of marker gene expression when compared to gene expression in a non-striatal spheroid, e.g. a cortical spheroid (hCS), when calculated using a standard statistical test.

To promote differentiation of neural progenitors into neurons, about 1 week, about 2 weeks, about 3 weeks, about 4 weeks after exposure to the inhibitor of the Wnt pathway and the recombinant activin A the neural medium is changed to replace the inhibitor of the Wnt pathway and the recombinant activin A (and the RXR agonist, if present) with an effective dose of BDNF and NT3. The growth factors can be provided at a concentration for each of at least about 0.5 ng/ml, at least about 1 ng/ml, at least about 5 ng/ml, at least about 10 ng/ml, at least about 20 ng/ml, up to about 500 ng/ml, up to about 250 ng/ml, up to about 100 ng/ml, or about 20 ng/ml.

The neural medium at this stage may be further supplemented with an effective dose of one or more of the following: a gamma secretase inhibitor, e.g. DAPT at a concentration of from about 1 to 25 μM, about 2 to 10 μM, and may be around about 2.5 μM; L-ascorbic acid at a concentration of from about 10 to 500 nM, from about 50 to 250 nM, and may be about 200 nM; cAMP at a concentration of from about 10 to 500 nM, from about 50 to 150 nM, and may be about 100 nM; and Docosahexaenoic acid (DHA). In some embodiments, the neural medium comprises an effective dose of BDNF, NT3, a gamma secretase inhibitor, L-ascorbic acid, cAMP and DHA.

About 4 weeks, about 5 weeks, about 6 weeks, about 7 weeks after exposure to the inhibitor of the Wnt pathway and the recom binant activin A, the spheroids can be maintained for extended periods of time in neural medium, e.g. for periods of 1, 2, 3, 4, 5, 6, 7, 8, 9, 10, 11, 12 months or longer. In some embodiments, the spheroids are maintained for a period of 3 months or longer. The spheroids may be maintained in a neural medium in the absence of growth factors.

The human striatal spheroids comprise functional GABAergic medium spiny neurons that develop dendritic spines after culture for an extended period of time in neural medium. As mentioned above, medium spiny neurons constitute the principal cell type in the human striatum and receive glutamatergic inputs from several areas including the cortex as well as dopaminergic inputs from the midbrain. The presence of dendritic spines can be determined by observation, e.g. through microscopy. The presence of GABAergic neurons can also be detected by monitoring reporter genes expressed using regulatory sequences (e.g. promoters and/or enhancers) that are specific for GABAergic neurons, such as Dlx. The functionality of the neurons can be determined by monitoring neuronal activity, e.g. by imaging $Ca^{2+}$ activity.

Human Cortical Spheroids.

Human cortical spheroids may be generated by the methods previously described, for example in Pasca et al. (2015) Nat. Methods 12(7):671-678, entitled "Functional cortical neurons and astrocytes from human pluripotent stem cells in 3D culture", herein specifically incorporated by reference.

For example, a suspension culture of hiPS cells is cultured to provide a neural progenitor spheroid, as described above. After about 5 days, about 6 days, about 7 days, about 8 days, about 9 days, about 10 days in suspension culture, the floating neural progenitor spheroids are moved to neural media to differentiate the neural progenitors. The media is supplemented with an effective dose of FGF2 and EGF. The growth factors can be provided at a concentration for each of at least about 0.5 ng/ml, at least about 1 ng/ml, at least about 5 ng/ml, at least about 10 ng/ml, at least about 20 ng/ml, up to about 500 ng/ml, up to about 250 ng/ml, up to about 100 ng/ml.

To promote differentiation of neural progenitors into hCS, comprising glutamatergic neurons, after about 1 week, about 2 weeks, about 3 weeks, about 4 weeks after FGF2/EGF exposure the neural medium is changed to replace the FGF2 and EGF with an effective dose of BDNF and NT3. The growth factors can be provided at a concentration for each of at least about 0.5 ng/ml, at least about 1 ng/ml, at least about 5 ng/ml, at least about 10 ng/ml, at least about 20 ng/ml, up to about 500 ng/ml, up to about 250 ng/ml, up to about 100 ng/ml. The cortical spheroids comprise functional glutamatergic neurons.

Midbrain Spheroids.

Generation of human midbrain spheroids (hMbS) (also named mibrain organoids) utilizes a similar multi-step process as for hStrS generation described above, with the use of agents to promote midbrain, rather than striatal, differentiation. Early spheroids induced to a neural fate by addition of effective dose of an inhibitor of BMP and of TGFβ pathways to the medium may be cultured in the presence of FGF8 and a sonic hedgehog pathway agonist, e.g. at the time of addition of the inhibitors of the BMP and TGFβ pathways, after about 12 hours, after about 24 hours, after about 1 day, after about 2 days, after about 3 days, after about 4 days of culture with the inhibitors of the BMP and TGFβ pathways. FGF8 and sonic hedgehog pathway agonist are maintained fora period of about 6 hours, about 12 hours, about 1 day, about 36 hours, about 2 days. FGF8 may be maintained for example at a concentration of from about 20 ng/ml to about 200 ng/ml, may be from about 50 ng/ml to about 150 ng/ml, may be from about 75 ng/ml to about 125 ng/ml, or may be about 100 ng/ml, depending on the activity of the inhibitor that is selected. The sonic hedgehog pathway agonist may be maintained for example at a concentration from about 0.1 μM to about 10 μM, from about 0.5 μM to about 5 μM, from about 0.5 μM to about 2 μM, or may be about 1 μM depending on the activity of the inhibitor that is selected.

Suitable sonic hedgehog pathway agonists include smoothened agonist, SAG, CAS 364590-63-6, which modulates the coupling of Smo with its downstream effector by interacting with the Smo heptahelical domain ($K_D$=59 nM). SAG may be provided in the medium at a concentration of from about 0.1 μM to about 10 μM, from about 0.5 μM to about 5 μM, from about 0.5 μM to about 2 μM, or may be about 1 μM.

The neural spheroids are then moved to neural medium and cultured in the presence of FGF8, a sonic hedgehog pathway agonist, an inhibitor of BMP and an inhibitor of GSK-3. The FGF8 and sonic hedgehog pathway agonist may be as described for step (a) above. The inhibitor of BMP may be LDN-193189 (J Clin Invest, 2015, 125(2):796-808); Galunisertib (LY2157299) (Cancer Res, 2014, 74(21):5963-77); LY2109761 (Toxicology, 2014, 326C:9-17); SB525334 (Cell Signal, 2014, 26(12):3027-35); SD-208; EW-7197; Kartogenin; DMH1; LDN-212854; M L347; LDN-193189 HCl (Proc Natl Acad Sci USA, 2013, 110(52):E5039-48); SB505124; Pirfenidone (Histochem Cell Biol, 2014, 10.1007/s00418-014-1223-0); RepSox; K02288; Hesperetin; GW788388; LY364947, etc. In certain embodiments, the inhibitor of BMP is LDN-193189 provided in the medium for example at a concentration from about 10 nM to about 500 nM, from about 50 nM to about 250 nM, from about 75 nM to about 125 nM, or may be about 100 nM. The inhibitor of GSK-3 may be CHIR 99021 added for example at a concentration of from about 0.5 μM to about 50 μM, about 1 μM to about 25 μM, about 1 μM to about 10 μM, about 1 μM to about 5 μM, or may be about 3 μM.

In order to provide a midbrain spheroid, the neural spheroids may be cultured in the neural medium for between about 1 and 4 weeks, between about 1 and 3 weeks, between about 2 and 3 weeks, during which time the FGF8 and sonic hedgehog pathway agonist may be present in the neural medium, or may be added to the neural medium after about 1, 2, or 3 days following transfer to the neural medium. The FGF8 and sonic hedgehog pathway agonist may be maintained in the neural medium for a period of between about 7 days and about 21 days, between about 7 days and about 18 days, between about 10 days and 18 days, about 7 days, about 10 days, about 14 days, about 18 days or about 21 days in the neural medium. The inhibitor of BMP may be added to the neural medium at the same time as the FGF8 and sonic hedgehog pathway agonist and may be maintained in the neural medium for a period of between about 7 days and about 14 days, between about 7 days and about 10 days, about 7 days, about 8 days, about 9 days, or about 10 days. The inhibitor of GSK-3 may be added to the neural medium at the same time as the FGF8 and sonic hedgehog pathway agonist or may be added to the neural medium after about 1, 2, or 3 days following FGF8 and sonic hedgehog pathway agonist addition. The inhibitor of GSK-3 may be maintained in the neural medium for a period of between about 7 days and 21 days, between about 10 days and 18 days, between about 12 days and 16 days, about 7 days, about 10 days, about 15 days, or about 20 days.

In certain embodiments, the neural spheroid is cultured in the neural medium for between about 2 and 3 weeks, where the inhibitor of FGF8 and sonic hedgehog pathway agonist is present in the neural medium after be present in the neural medium, or are be added to the neural medium after about 1 day, and are maintained in the neural medium fora period of between about 10 days and 18 days; the inhibitor of BMP is added to the neural medium at the same time as the FGF8 and sonic hedgehog pathway agonist, and is maintained in the neural medium for a period of between about 7 days and about 10 days; and the inhibitor of GSK-3 is added to the neural medium after about 1 day following FGF8 and sonic hedgehog pathway agonist addition, and is maintained in the neural medium for a period of between about 12 days and 16 days.

As demonstrated in the examples, the combined use of FGF8, sonic hedgehog pathway agonist, inhibitor of BMP and inhibitor of GSK-3 results in the formation of midbrain spheroids with high levels of markers indicative of the human midbrain, e.g. at least 3 weeks after the suspension culture of hiPS cells was induced to a neural fate. For example, the midbrain spheroids may have high levels of floor plate mesencephalic dopaminergic neurons markers such as EN1 and FOX/12 and low levels of forebrain markers such as FOXG1. Methods for determining levels of marker genes include qPCR as further described in examples. In some embodiments, the methods disclosed herein further comprise determining whether the midbrain spheroids express markers indicative of the human midbrain. A midbrain spheroid having high or low levels of a marker gene may have a significantly higher or lower level of marker gene expression when compared to gene expression in a non-midbrain spheroid, e.g. a cortical spheroid, when calculated using a standard statistical test.

To promote differentiation of neural progenitors into neurons, about 1 week, about 2 weeks, about 3 weeks, about 4 weeks after exposure to FGF8, sonic hedgehog pathway agonist, inhibitor of BMP and inhibitor of GSK-3, the neural medium is changed to replace the FGF8, sonic hedgehog pathway agonist, inhibitor of BMP and inhibitor of GSK-3 with an effective dose of BDNF and NT3. The growth factors can be provided at a concentration for each of at least about 0.5 ng/ml, at least about 1 ng/ml, at least about 5 ng/ml, at least about 10 ng/ml, at least about 20 ng/ml, up to about 500 ng/ml, up to about 250 ng/ml, up to about 100 ng/ml. The neural medium at this stage may be further supplemented with one or more of the following: a gamma secretase inhibitor, e.g. DAPT at a concentration of from about 1 to 25 μM, about 2 to 10 μM, and may be around about 2.5 μM; L-ascorbic acid at a concentration of from about 10 to 500 nM, from about 50 to 250 nM, and may be about 200 nM; cAMP at a concentration of from about 10 to 500 nM, from about 50 to 150 nM, and may be about 100 nM; and DHA.

The midbrain spheroids may be can be maintained in the supplemented neural medium for about 1 week, about 2 weeks, about 3 weeks. After such culture, the midbrain spheroids can be maintained for extended periods of time in neural medium, e.g. for periods of 1, 2, 3, 4, 5, 6, 7, 8, 9, 10, 11, 12, 24, 36 months or longer. In some embodiments, the spheroids are maintained for a period of 3 months or longer. The spheroids may be maintained in a neural medium in the absence of growth factors. The human midbrain spheroids comprise dopaminergic neurons after culture for an extended period of time in neural medium.

Assembloids. The hStrS can be functionally integrated with separately cultured human cortical spheroids (hCS), to form cortico-striatal assembloids (hCS-hStrS) which include glutamatergic neurons. The resulting hCS-hStrS contains cortico-striatal circuits and provides for functional integration of these circuits. Functionally integrated cells interact in a physiologically relevant manner, e.g. forming synapses or neuromuscular junctions, transmitting signals, forming multicellular structures, and the like.

The cortical spheroids are co-cultured with the human striatal spheroids in neural medium under conditions permissive for cell fusion. Condition permissive for cell fusion may include culturing the hStrS and hCS in close proximity, e.g. in direct contact with one another.

Assembly may be performed with spheroids after around about 30 days, about 60 days, about 90 days of culture for hStrS; and after around about 30 days, about 60 days, about 90 days of culture for hCS. The hStrS and hCS spheroids may be co-cultured for a period of 3 days, 5 days, 8 days, 10 days, 14 days, 18 days, 21 days or more. The resulting cortico-striatal assembloids are demonstrated to contain functional neural circuits, where the assembloids comprise glutamatergic neurons projecting from the hCS to the hStrS. The glutamatergic neurons may be unidirectional neurons, for example unidirectional CTIP2 and/or SATB2 expressing neurons. Methods for confirming the functionality of the neurons are known in the art and include optogenetic methods and imaging of calcium activity in neurons, such as those methods described in the examples. In some embodiments, the methods may comprise confirming the functionality of the neurons in the cortico-striatal assembloid.

Human Midbrain Spheroids (hMbS) and Midbrain-Striatal Assembloids (hMbS-hStrS)

As described above, the human striatum receives dopaminergic input from the midbrain, which play an important role in the development and maturation of the striatum. Additionally, GABAergic modulation of the midbrain from the striatum is an essential component of the basal ganglia direct pathway. In order to study these circuits, the hMbS can be functionally integrated with separately cultured hStrS to form midbrain-striatal assembloids (hMbs-hStrS), which include dopaminergic neurons and GABAergic medium spiny neurons. The resulting hMbS-hStrS assembloids provide for functional integration of the midbrain-striatal circuits.

The hMbS and hStrS are generated separately as described herein and then co-cultured in neural medium under conditions permissive for cell fusion. Condition permissive for cell fusion may include culturing the hMbS and hStrS in close proximity, e.g. in contact with one another.

Assembly may be performed with spheroids after around about 30 days, about 60 days, about 90 days of culture for hStrS; and after around about 30 days, about 60 days, about 90 days of culture for hMbS. The hStrS and hMbS spheroids may be co-cultured for a period of 1 day, 2 days, 3 days or more. The resulting hMbS-hStrS contain functional neural circuits, where the hMbs-hStrS assembloids comprise midbrain neurons (e.g. dopaminergic neurons) projecting from hMbS to hStrS.

The spheroids described above can be further assembled into three-part cortico-striatal-midbrain assembloids (hCS-hStrS-hM bS) to study neural circuits involving neurons of the striatum, cortex and midbrain. For example, the hCS-hStrS assembloids described above can be co-cultured with hMbS to provide these three-part assembloids. Alternatively, the hMbS-hStrS described above can be co-cultured with hCS to provide the three-part assembloids. Further alternatively, the hMbS, hStrS and hCS spheroids can be separately generated and all three spheroids co-cultured to provide the three-part assembloids. The resulting three-part assembloids comprise dopaminergic neurons projecting from hMbS to hStrS and glutamatergic neurons projecting from the hCS to hStrS and can be used to study glutamatergic and dopaminergic modulation in this system.

Screening Assays

Also disclosed herein are screening assays which involve determining the effect of a candidate agent on the spheroid, e.g. hStrS or hMbS, or assembloid, e.g. hCS-hStrS; hMbs-hStrS; or hCS-hStrS-hMbS, or a cell derived therefrom. A candidate agent may be a small molecule or a genetic agent. The screening assays may involve contacting the candidate agent with the spheroid, assembloid or cell derived therefrom and determining effect of the candidate agent on a parameter of the spheroid, assembled or cell, where such parameters include morphologic, genetic or functional changes.

For example, a screening assay may involve determining the effect that a candidate agent has on the number and/or functionality of neural circuits within a spheroid or assembloid. As described herein, hCS-hStrS assembloids normally comprise neurons projecting from the hCS to the hStrS and that these neurons are functional. The screening assays may therefore involve determining whether a candidate agent is able to increase or reduce the num berand/or functionality of these cortico-striatal circuits in assembloids comprising hCS and hStrS. As also described herein, hMbS-hStrS assembloids comprise neurons projecting from the hMbS to the hStrS. The screening assays may therefore involve determining whether a candidate agent is able to increase or reduce the number and/or functionality of these striato-midbrain circuits in assembloids comprising hMbS and hStrS.

As also described herein, various diseases and disorders are associated with cortico-striatal dysfunction. Accordingly, the assays described herein may find particular utility where the spheroid or assembloid comprise at least one allele associated with a neurologic or psychiatric disorder, such as schizophrenia, obsessive-compulsive disorder, Tourette syndrome, Huntington's disease, Parkinson's disease and autism spectrum disorder. Candidate agents that are able to restore the functionality of cortico-striatal circuits in spheroids or assembloids comprising these disorder-associated alleles may have therapeutic utility in the treatment of said disorder.

Neural activity causes rapid changes in intracellular free calcium. Calcium imaging assays that exploit this can therefore be used to determine the functional of neuronal circuits. This may involve modifying neurons to contain genetically-encoded calcium indicator proteins, such those proteins that include the fluorophore sensor GCaMP and imaging those cells. GCaMP comprises a circularly permuted green fluorescent protein, a calcium-binding protein calmodulin (CaM) and CaM-interacting M13 peptide, where brightness of the GFP increases upon calcium binding. Further details about calcium imaging assays are described in Chen et al. (2013) Nature 499(7458): 295-300. Other calcium imaging assays include Fura-2 calcium imaging; Fluo-4 calcium imaging, and Cal-590 calcium imaging.

For example, the neurons may be modified to express GCaMP6f. This can be combined with methods that activate certain neurons in response to external stimuli, for example optogenetic methods that activate neurons in response to light. For example, to test functionality between two types of neurons involved in a neural circuit, a "first" neuron can be modified to express an optogenetic actuator (e.g. Chrim sonR) and a "second" neuron modified to express a calcium indicator (e.g. GCaMP6f) and imaging used to monitor calcium release. If the first neuron is functionally connected (synapses with) the second neuron then optogenetic activation of the first neuron will elicit calcium release and a visible readout in the second neuron. As set out in the Examples herein, such a method was used to confirm functionality of the cortico-striatal circuits.

Methods of analysis at the single cell level are also of interest, e.g. as described above: live imaging (including confocal or light-sheet microscopy), single cell gene expression or single cell RNA sequencing, calcium imaging, immunocytochemistry, patch-clamping, flaw cytometry and the like. Various parameters can be measured to determine the effect of a drug or treatment on the spheroids, assembloids or cells derived therefrom. For example, single cell RNA sequencing of the cells that make up the spheroid or assembloid can be used to characterize the identity of these cells and can be utilized in assays that aim to determine whether a candidate agent affects cell identity.

Parameters are quantifiable components of cells, particularly components that can be accurately measured, desirably in a high throughput system. A parameter can also be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Variability is expected and a range of values for each of the set of test parameters will be obtained using standard statistical methods with a common statistical method used to provide single values.

Parameters of interest include detection of cytoplasmic, cell surface or secreted biomolecules, biopolymers, e.g. polypeptides, polysaccharides, polynucleotides, lipids, etc. Cell surface and secreted molecules are a preferred parameter type as these mediate cell communication and cell effector responses and can be more readily assayed. In one embodiment, parameters include specific epitopes. Epitopes are frequently identified using specific monoclonal antibodies or receptor probes. In some cases, the molecular entities comprising the epitope are from two or more substances and comprise a defined structure; examples include combinatorically determined epitopes associated with heterodimeric integrins. A parameter may be detection of a specifically modified protein or oligosaccharide. A parameter may be defined by a specific monoclonal antibody or a ligand or receptor binding determinant.

Candidate agents of interest are biologically active agents that encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, New York, (1996), Ninth edition, under the sections: Drugs Acting at Synaptic and NeuroeffectorJ unctional Sites; Cardiovascular Drugs; Vitamins, Dermatology; and Toxicology, all incorporated herein by reference.

Test compounds include all of the classes of molecules described above and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also include the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As used herein, the term "genetic agent" refers to polynucleotides and analogs thereof, which agents are tested in the screening assays of the invention by addition of the genetic agent to a cell. The introduction of the genetic agent results in an alteration of the total genetic composition of the cell. Genetic agents such as DNA can result in an experimentally introduced change in the genome of a cell, generally through the integration of the sequence into a chromosome, for example using CRISPR mediated genomic engineering (see for example Shmakov et al. (2017) Nature Reviews Microbiology 15:169). Genetic changes can also be transient, where the exogenous sequence is not integrated but is maintained as an episomal agents. Genetic agents, such as antisense oligonucleotides, can also affect the expression of proteins without changing the cell's genotype, by interfering with the transcription or translation of m RNA. The effect of a genetic agent is to increase or decrease expression of one or more gene products in the cell.

Introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an anti-sense oligonucleotide; RNAi, encode a dominant negative mutation, or dominant or constitutively active mutations of native sequences; altered regulatory sequences, etc. The expression vector may be a viral vector, e.g. adeno-associated virus, adenovirus, herpes simplex virus, retrovirus, lentivirus, alphavirus, flavivirus, rhabdovirus, measles virus, Newcastle disease virus, poxvirus and picornavirus vectors.

Antisense and RNAi oligonucleotides can be chemically synthesized by methods known in the art. Preferred oligonucleotides are chemically modified from the native phosphodiester structure, in order to increase their intracellular stability and binding affinity. A number of such modifications have been described in the literature, which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity, e.g. morpholino oligonucleotide analogs.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of selected parameters, in addition to the functional parameters described above. For measuring the amount of a molecule that is present, a convenient method is to label a molecule with a detectable moiety, which may be fluorescent, luminescent, radioactive, enzymatically active, etc., particularly a molecule specific for binding to the parameter with high affinity fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to fluoresce, e.g. by expressing them as green fluorescent protein chimeras inside cells (for a review see Jones et al. (1999) Trends Biotechnol. 17(12):477-81). Thus, antibodies can be genetically modified to provide a fluorescent dye as part of their structure Depending upon the label chosen, parameters may be measured using other than fluorescent labels, using such immunoassay techniques as radioimmunoassay (RIA) or enzyme linked immunosorbant assay (ELISA), homogeneous enzyme immunoassays, and related non-enzymatic techniques. These techniques utilize specific antibodies as reporter molecules, which are particularly useful due to their high degree of specificity for attaching to a single molecular target. U.S. Pat. No. 4,568,649 describes ligand detection systems, which employ scintillation counting. These techniques are particularly useful for protein or modified protein parameters or epitopes, or carbohydrate determinants. Cell readouts for proteins and other cell determinants can be obtained using fluorescent or otherwise tagged reporter molecules. Cell based ELISA or related non-enzymatic or fluorescence-based methods enable measurement of cell surface parameters and secreted parameters. Capture ELISA and related non-enzymatic methods usually employ two specific antibodies or reporter molecules and are useful for measuring parameters in solution. Flow cytometry methods are useful for measuring cell surface and intracellular parameters, as well as shape change and granularity and for analyses of beads used as antibody- or probe-linked reagents. Readouts from such assays may be the mean fluorescence associated with individual fluorescent antibody-detected cell surface molecules or cytokines, or the average fluorescence intensity, the median fluorescence intensity, the variance in fluorescence intensity, or some relationship among these.

Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

The results of an assay can be entered into a data processor to provide a dataset. Algorithms are used for the comparison and analysis of data obtained under different conditions. The effect of factors and agents is read out by determining changes in multiple parameters. The data will include the results from assay combinations with the agent (s), and may also include one or more of the control state, the simulated state, and the results from other assay combinations using other agents or performed under other conditions. For rapid and easy comparisons, the results may be presented visually in a graph, and can include numbers, graphs, color representations, etc.

The dataset is prepared from values obtained by measuring parameters in the presence and absence of different cells, e.g. genetically modified cells, cells cultured in the presence of specific factors or agents that affect neuronal function, as well as comparing the presence of the agent of interest and at least one other state, usually the control state, which may include the state without agent or with a different agent. The parameters include functional states such as synapse formation and calcium ions in response to stimulation, whose levels vary in the presence of the factors. Desirably, the results are normalized against a standard, usually a "control value or state," to provide a normalized data set. Values obtained from test conditions can be normalized by subtracting the unstimulated control values from the test values, and dividing the corrected test value by the corrected stimulated control value. Other methods of normalization can also be used; and the logarithm or other derivative of measured values or ratio of test to stimulated or other control values may be used. Data is normalized to control data on the same cell type under control conditions, but a dataset may comprise normalized data from one, two or multiple cell types and assay conditions.

The dataset can comprise values of the levels of sets of parameters obtained under different assay combinations. Compilations are developed that provide the values for a sufficient number of alternative assay combinations to allow comparison of values.

A database can be compiled from sets of experiments, for example, a database can contain data obtained from a panel of assay combinations, with multiple different environmental changes, where each change can be a series of related compounds, or compounds representing different classes of molecules.

Mathematical systems can be used to compare datasets, and to provide quantitative measures of similarities and differences between them. For example, the datasets can be analyzed by pattern recognition algorithms or clustering methods (e.g. hierarchical or k-means clustering, etc.) that use statistical analysis (correlation coefficients, etc.) to quantify relatedness. These methods can be modified (by weighting, employing classification strategies, etc.) to optimize the ability of a dataset to discriminate different functional effects. For example, individual parameters can be given more or less weight when analyzing the dataset, in order to enhance the discriminatory ability of the analysis. The effect of altering the weights assigned each parameter is assessed, and an iterative process is used to optimize pathway or cellular function discrimination.

The comparison of a dataset obtained from a test compound, and a reference dataset(s) is accomplished by the use of suitable deduction protocols, AI systems, statistical comparisons, etc. Preferably, the dataset is compared with a database of reference data. Similarity to reference data involving known pathway stimuli or inhibitors can provide an initial indication of the cellular pathways targeted or altered by the test stimulus or agent.

A reference database can be compiled. These databases may include reference data from panels that include known agents or combinations of agents that target specific pathways, as well as references from the analysis of cells treated under environmental conditions in which single or multiple environmental conditions or parameters are removed or specifically altered. Reference data may also be generated from panels containing cells with genetic constructs that selectively target or modulate specific cellular pathways. In this way, a database is developed that can reveal the contributions of individual pathways to a complex response.

The effectiveness of pattern search algorithms in classification can involve the optimization of the number of parameters and assay combinations. The disclosed techniques for selection of parameters provide for computational requirements resulting in physiologically relevant outputs. Moreover, these techniques for pre-filtering data sets (or potential data sets) using cell activity and disease-relevant biological information improve the likelihood that the outputs returned from database searches will be relevant to predicting agent mechanisms and in vivo agent effects.

For the development of an expert system for selection and classification of biologically active drug compounds or other interventions, the following procedures are employed. For every reference and test pattern, typically a data matrix is generated, where each point of the data matrix corresponds to a readout from a parameter, where data for each parameter may come from replicate determinations, e.g. multiple individual cells of the same type. As previously described, a data point may be quantitative, semi-quantitative, or qualitative, depending on the nature of the parameter.

The readout may be a mean, average, median or the variance or other statistically or mathematically derived value associated with the measurement. The parameter readout information may be further refined by direct comparison with the corresponding reference readout. The absolute values obtained for each parameter under identical conditions will display a variability that is inherent in live biological systems and also reflects individual cellular variability as well as the variability inherent between individuals.

Classification rules are constructed from sets of training data (i.e. data matrices) obtained from multiple repeated experiments. Classification rules are selected as correct,/ identifying repeated reference patterns and successfully distinguishing distinct reference patterns. Classification rule-learning algorithms may include decision tree methods, statistical methods, naive Bayesian algorithms, and the like.

A knowledge database will be of sufficient complexity to permit novel test data to be effectively identified and classified. Several approaches for generating a sufficient,/encompassing set of classification patterns, and sufficiently powerful mathematical/statistical methods for discriminating between them can accomplish this.

The data from cells treated with specific drugs known to interact with particular targets or pathways provide a more detailed set of classification readouts. Data generated from cells that are genetically modified using over-expression techniques and anti-sense techniques, permit testing the influence of individual genes on the phenotype.

A preferred knowledge database contains reference data from optimized panels of cells, environments and parameters. For complex environments, data reflecting small variations in the environment may also be included in the knowledge database, e.g. environments where one or more factors or cell types of interest are excluded or included or quantitatively altered in, for example, concentration or time of exposure, etc For further elaboration of general techniques useful in the practice of this invention, the practitioner can refer to standard textbooks and reviews in cell biology, tissue culture, embryology, and neurobiology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Each publication cited in this specification is hereby incorporated by reference in its entirety for all purposes.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Experimental

Described herein is a novel approach to study functional neuromodulatory systems using human pluripotent stem cells (hPSCs) to generate three-dimensional (3D) assembloids that contain midbrain and corticostriatal assembloids. We generated hiPS cells-derived human striatum spheroids (hStrS), which include functional GABAergic medium spiny neurons that develop dendritic spines after 3-4 months culture. We also generated midbrain spheroids. This work involved identifying new combinations of small molecules and growth factors required for in vitro generation of these structures. Assembly of hStrS with human cortical spheroids (hCS), which include pyramidal glutamatergic neurons that project to striatum, results in the formation of unidirectional corticostriatal projections in assembloids and enables unique functional features. Moreover, this preparation can be further assembled with midbrain spheroids to create a three-part assembloids in which both glutamatergic and dopaminergic modulation can be tested. Using a combination of viral tracing (including G-deleted rabies virus), optogenetics coupled with live calcium imaging, we present evidence of the formation of a functional in vitro model of the human corticostriatal circuits, which can be used as a platform for modeling disease as well as for testing therapeutics (including gene therapy and small molecule drugs).

Example 1

Methods

Generation of human striatum spheroids (hStrS). Human induced pluripotent stem (hiPS) cells were cultured on vitronectin-coated plates (5 μg $ml^{-1}$, Thermo Fisher Scientific, A14700) in Essential 8 medium (Thermo Fisher Scientific, A1517001). Cells were passaged every 4 days with UltraPure™ 0.5 mM EDTA, pH 8.0 (Thermo Fisher Scientific, 15575). For the generation of 3D neural spheroids, hiPS cells were incubated with Accutase® (Innovative Cell Technologies, AT104) at 37° C. for 7 min and dissociated into single cells. Optionally, 1 day before spheroid formation, hiPS cells can be exposed to 1% dimethyl sulfoxide (DMSO) (Sigma-Aldrich, 472301) in Essential 8 medium. To obtain uniformly sized spheroids, AggreWell-800 (STEMCELL Technologies, 34815) containing 300 microwells was used. Approximately $3\times10^6$ single cells were added per AggreWell-800 well in Essential 8 medium supplemented with the ROCK inhibitor Y27632 (10 μM, Selleckchem, S1049), centrifuged at 100 g for 3 min to capture the cells in the microwells, and incubated at 37° C. with 5% $CO_2$. After 24 h, spheroids consisting of approximately 10,000 cells were collected from each microwell by pipetting medium in the well up and down with a cut P1000 pipet tip and transferred into ultra-low attachment plastic dishes (Corning, 3262) in Essential 6 medium (Thermo Fisher Scientific, A1516401) supplemented with two SMAD pathway inhibitors—dorsomorphin (2.5 μM, Sigma-Aldrich, P5499) and SB-431542 (10 μM, R&D Systems, 1614). For the first 5 d, Essential 6 medium was changed every day and supplemented with dorsomorphin and SB-431542. Optionally, the Wnt pathway inhibitor XAV-939 (2.5 μM, Tocris, 3748) can be added with the two SMAD pathway inhibitors.

To generate hStrS, on day 6 in suspension the spheroids were transferred to neural medium containing Neurobasal™-A Medium (Thermo Fisher Scientific, 10888022), B-27™ Supplement, minus vitamin A (Thermo Fisher Scientific, 12587010), GlutaMAX™ Supplement (1:100, Thermo Fisher Scientific, 35050079), Penicillin-Streptomycin (1:100, Thermo Fisher Scientific, 15070063), and supplemented with the Wnt pathway inhibitor IWP-2 (2.5 μM, Selleckchem, S7085) and Recombinant Human/Murine/Rat Activin A (50 μg $ml^{-1}$, PeproTech, 120-14P). On day 11 of differentiation, spheroids were supplemented with the pan retinoid X receptor (RXR) agonist, SR11237 (100 nM, Tocris, 3411), in addition to the compounds described above.

From day 23, to promote differentiation of the neural progenitors into neurons, the neural medium was supplemented with brain-derived neurotrophic factor (BDNF; 20 ng $ml^{-1}$, PeproTech, 450-02), NT3 (20 ng ml-1, PeproTech, 450-03), L-Ascorbic Acid 2-phosphate Trisodium Salt (AA; 200 nM, Wako, 323-44822), N6, 2'-O-Dibutyryladenosine 3',5'-cycic monophosphate sodium salt (cAMP; 100 μM, Millipore Sigma, D0627), cis-4, 7, 10, 13, 16, 19-Docosahexaenoic acid (DHA; Millipore Sigma, D2534). From day 43, the neural medium was supplemented with 2.5 μM DAPT (STEMCELL Technologies, 72082) in addition to the BDNF, NT3, AA, cAMP. From day 47, only neural medium containing B-27™ Supplement, minus vitamin A (Thermo Fisher Scientific, 12587010) or B-27™ Plus Supplement (Thermo Fisher Scientific, A3582801) was used for medium changes every 4 days.

Real-time qPCR. m RNA was isolated using the RNeasy Mini Kit (Qiagen, 74106) and DNase I, Amplification Grade (Thermo Fisher Scientific, 18068-015), and template cDNA was prepared by reverse transcription using the SuperScript™ III First-Strand Synthesis SuperMbc for qRT-PCR (Thermo Fisher Scientific, 11752250). qPCR was performed using SYBR™ Green PCR Master Mix (Thermo Fisher Scientific, 4312704) on a ViiA7 Real-Time PCR System (Thermo Fisher Scientific, 4453545).

Cryoprotection and immunofluorescence staining. hCS, hStrS and cortico-striatal assembloids were fixed in 4% paraformaldehyde (PFA)/phosphate buffered saline (PBS) overnight at 4° C. They were then washed in PBS and transferred to 30% sucrose/PBS for 2-3 days until the spheres/assembloids sink in the solution. Subsequently, they were rinsed in optimal cutting temperature (OCT) compound (Tissue-Tek OCT Compound 4583, Sakura Finetek) and 30% sucrose/PBS (1:1), and embedded. For immunofluorescence staining, 18 μm-thick sections were cut using a Leica Cryostat (Leica, CM 1850). Cryosections were washed with PBS to remove excess OCT on the sections and blocked in 10% Normal Donkey Serum (NDS, Abcam, ab7475), 0.3% Triton X-100 (Millipore Sigma, T9284-100ML), 1% BSA diluted in PBS for 1 h at room temperature. The sections were then incubated overnight at 4° C. with primary antibodies diluted in PBS containing 2% NDS, 0.1% Triton X-100. PBS was used to wash the primary antibodies and the cryosections were incubated with secondary antibodies in PBS with the PBS containing 2% NDS, 0.1% Triton X-100 for 1 h. Dissociated cultures on glass coverslips were fixed in 4% PFA/4% sucrose in PBS for 20 min at 37° C. and then rinsed for 5 min with PBS twice. The coverslips were blocked in 10% Normal Donkey Serum (NDS, Abcam, ab7475), 0.3% Triton X-100 (Millipore Sigma, T9284-100ML), 1% BSA diluted in PBS for 1 h at room temperature, and then incubated overnight at 4C with primary antibodies diluted in PBS containing 2% NDS, 0.1% Triton X-100. PBS was used to wash the primary antibodies and the cryosections were incubated with secondary antibodies in PBS with 2% NDS, 0.1% Triton X-100.

The following primary antibodies were used for staining: anti-CTIP2 (rat, Abcam, ab18465), anti-DARPP32 (rabbit, Cell Signaling Technology, 2306S), anti-DARPP32 (rabbit, Abcam, ab40801), anti-GAD67 (mouse, Millipore Sigma, MAB5406), anti-NeuN (mouse, Abcam, ab104224), anti-GFP (chicken, GeneTex, GTX13970), anti-m Cherry (rabbit, GeneTex, GTX128508), anti-MAP2 (guinea pig, Synaptic Systems 188 004), anti-GFAP (rabbit, DAKO, Z0334), anti-SATB2 (mouse, Abcam, ab51502). Alexa Fluor dyes (Life Technologies) were used at 1:1,000 dilution, and nuclei were visualized with Hoechst 33258 (Life Technologies, H3549). Cryosections were mounted for microscopy on glass slides using Aquamount (Polysciences, 18606), and imaged on a Leica TCS SP8 confocal microscope. Images were processed in Fiji (NIH).

Single cell RNA-seg library preparation and data analysis. In order to obtain single cell suspension, hStrS or hMbS were dissociated using the papain (Worthington Biochemical, LS003119). hStrS or hMbS were collected into 1.5 mL Eppendorf tube with papain solution and incubated in 37° C. incubator for 15 min with gentle shaking every 5 min. Papain was inactivated with 10% FBS in neurobasal media, and hStrS were gently triturated using pipet tips, and then suspended in 0.04% BSA/PBS (Millipore-Sigma, B6917-25MG) at concentration of 1,000 cells//./L. Total 10,000 cells were loaded, and cDNA library was generated with the Chromium$^{1M}$ Single Cell 3' Library & Gel Bead kit v3 (10× Genomics, PN-1000154, PN-1000075) according to the manufacturer's instructions. Each library was sequenced using the Illumina NovaSeq S4 2×150 bp, mapped to human genome (hg38). Quality control, UMI counting of Ensemble genes and K-means clustering were performed by count function of Cellranger software (10× Genomics). Further downstream analyses were performed using the R package Seurat (version 3.1.4). Comparison of hStrS GABAergic neurons cluster data to BrainSpan transcriptomics data of miscro-dissected human brain tissue was performed using VoxHunt.

Viral labeling and five cell imaging. The viral infection of the 3D neural spheroids was performed as previously described (Birey et al., 2017) with minor modification. In brief, hCS or hStrS were transferred to a 1.5 mL Eppendorf tube containing 200 μL of culture mediirn with virus and incubated overnight at 37 C, 5% $CO_2$. Fresh 800 μL of culture media was added to the tube following day and incubated overnight. The next day, spheres were transferred into fresh culture media in ultra-low attachment plates. For the live cell imaging, the labeled spheres or assembloids were transferred to a well in a Corning™ 96-Well Half Area High Content Imaging Glass Bottom Microplate (Corning, 4580) in 150 μL of culture media and incubated in an environmentally controlled chamber for 15-30 min before imaging with Leica TCS SP8. The viruses used in this study are: AAV-mDIx-GFP-Fishell-1 (Addgene, #83900), AAV-Ple94 (GPR88)-iCre (pEMS1995, Addgene, #49125), AAV-DJ-EF1a-DIO-GCAMP6s (Stanford University Neuroscience Gene Vector and Virus Core, GWC-AAV-91), AAV-DJ-hSyn::eYFP (Stanford University Neuroscience Gene Vector and Virus Core, GWC-AAV-16), AAV-DJ-hSyn::mCherry (Stanford University Neuroscience Gene Vector and Virus Core, GVVC-AAV-17), Rabies-ΔG-Cre-eGFP (Salk institute Viral Vector Core), AAV-DJ-EF1a-CVS-G-WPRE-pG HpA (Addgene, #67528), AAV-DJ-EF1-DIO-mCherry (Stanford University Neuroscience Gene Vector and Virus Core, GWC-AAV-14), AAV1-hSyn::ChrimsonR-tdT (Addgene, #59171-AAV1), AAV9-rTH::Cre (Addgene, #107788-AAV9) and AAV-DJ-EF1a-DIO-eYFP (Stanford University Neuroscience Gene Vector and Virus Core, GWC-AAV-13). Several AAVs were generated at the Neuroscience Gene Vector and Virus Core at Stanford University School of Medicine or purchased from Addgene. Rabies-ΔG-viruses were purchased from the Salk institute Viral Vector Core.

Generation of cortico-striatal assembloids. In order to generate cortico-striatal (hCS-hStrS) assembloids, hCS and hStrS were generated separately, and later assembled by placing them in close proximity with each other in 1.5 ml microcentrifuge tubes for 3 days in an incubator. Media was carefully changed on day 2, and on the third day, assembloids were placed in 6-well or 60 mm ultralow attachment plates in the neural medium described above using a cut P1000 pipette tip. Afterthis, media was changed every 4 days. hCS was generated by previously described methods (Yoon et al., 2019) with minor modification. Assembly was performed at days (d) 60-80 of hCS and hStrS.

Projection imaging in intact cortico-striatalassembloids. The projection of hCS-derived AAV-DJ-hSynt:eYFP$^+$ cells into hStrS was imaged under environmentally controlled conditions in intact, cortico-striatal assembloids using Leica TCS SP8 confocal microscope with a motorized stage. Assembloids were transferred to a well in a Corning™ 96-Well Half Area High Content Imaging Glass Bottom Microplate (Corning, 4580) in 150 μL of culture media and incubated in an environmentally controlled chamber for 15-30 min before imaging. Images were taken using a 10× objective lens at a depth of 0-500 μm.

Retrograde neural tracing of cortico-striatal assembloids with ΔG-rabies virus. For retrograde neural tracing experiments of cortico-striatal assembloids with ΔG-Rabies virus, hCS were labeled with AAV-DJ-EF1-DIO-mCherry and hStrS were labeled with ΔG-Rabies-eGFP-Cre and AAV-DJ-EF1a-CVS-G-WPRE-pGHpA After viral infection, hCS and hStrS were assembled and maintained in culture with media changes every 4 days for 28 days. After 28 days, assembloids were fixed with 4% PFA/PBS for 20 min and processed for immunostaining.

Optogenetic stimulation and GCaMP6 imaging of assembloids. Intact assembloids were imaged under environmentally controlled conditions using a 10× objective lens with a Leica TCS SP8 confocal microscope. At a frame rate of 14.7 frames/sec, a stimulation experiments consisted of 500 frames acquired during pre-stimulation, 1 frame of 625 nm LED stimulation, and 1,000 frames acquired during post-stimulation. For optogenetic stimulation, a pulse of 625 nm LED light was delivered using an optical fiber-coupled LED (400 μm-diameter, 13.2 mW, Thorlabs) that was directed towards the hCS. The pulse was generated by a CYCLOPS LED driver coupled with the Leica TCS SP8.

Whole cell recordings. Spheroid or assembloid slices were embedded in 4% agarose, and transferred into an artificial cerebrospinal fluid (aCSF) containing 126 mM NaCl, 2.5 mM KCl, 1.25 mM $NaHPO_4$, 1 mM $MgSO_4$, 2 mM $CaCl_2$, 26 mM $NaHCO_3$ and 10 mM D-(+)-glucose. Slices were cut at 200 μm at room temperature using a Leica VT1200 vibratome and maintained in aCSF at room temperature. Whole-cell patch-clamp recordings from hStrS slices were performed under an upright slicescope microscope (Scientifica). Slices were perfused with aCSF (bubbled with 95% $O_2$ and 5% $CO_2$) and cells were recorded at rom temperature. hSyn1::eYFP labeled neurons were patched with a borosilicate glass pipette filled with an internal solution containing 127 mM potassium gluconate, 8 mM NaCl, 4 mM MgATP, 0.3 mM $Na_2GTP$, 10 mM HEPES, 0.6 mM EGTA, pH 7.2 adjusted with KOH (290 mOsm). Data were acquired with a MultiClamp 700B amplifier (Molecular Devices) and Digidata 1550B digitizer (Molecular Devices), low-pass filtered at 2 kHz and digitized at 20 kHz, analyzed with the pClamp software (version 10.6, Molecular Devices). The liquid junction potential was calculated using JPCalc, and recordings were corrected with an estimated −15 mM liquid junction potential. For F-I curves, cells were current-clamped at −60 mV, current steps (1s duration) were given with an increment of 10 pA.

Generation of human midbrain spheroids (hMbS) and midbrain-striatal assembloids (hMbS-hStrS). To generate hMbS, on day 3 in suspension the spheroids were supplemented with 100 ng/mL FGF8 (PeproTech, 100-25-100 μg) and 1 μM SAG (Millipore Sigma, 566660-1MG), in addition with two SMAD pathway inhibitors. For the first 5 d, Essential 6 medium was changed every day and supplemented with dorsomorphin and SB-431542. On day 6 in suspension the spheroids were transferred to neural medium containing Neurobasal™-A Medium (Thermo Fisher Scientific, 10888022), B-27™ Supplement, minus vitamin A (Thermo Fisher Scientific, 12587010), GlutaMAX™ Supplement (1:100, Thermo Fisher Scientific, 35050079), Penicillin-Streptomycin (1:100, Thermo Fisher Scientific, 15070063), and supplemented with the 100 ng/mL FGF8 (day 7-21), 1 μM SAG (day 7-21), 100 nM LDN (day 7-16, Selleckchem, S7507) and 3 μM CHIR (day 8-23). From day 23, to promote differentiation of the neural progenitors into neurons, the neural medium was supplemented with brain-derived neurotrophic factor (BDNF; 20 ng $ml_{-1}$, PeproTech, 450-02), NT3 (20 ng $ml_{-1}$, PeproTech, 450-03), L-Ascorbic Acid 2-phosphate Trisodium Salt (AA; 200 nM, Wako, 323-44822), N6, 2'-O-Dibutyryladenosine 3', 5'-cyclic monophosphate sodium salt (cAMP; 100 M, Millipore Sigma, D0627), cis-4, 7, 10, 13, 16, 19-Docosahexaenoic acid (DHA; Millipore Sigma, D2534). From day 43, the neural medium was supplemented with 2.5 μM DAPT (STEMCELL Technologies, 72082) in addition to the BDNF, NT3, AA, cAMP. From day 47, only neural medium containing B-27™ Supplement, minus vitamin A (Thermo Fisher Scientific, 12587010) or B-27™ Plus Supplement (Thermo Fisher Scientific, A3582801) was used for medium changes every 4 days. In order to generate meso-striatal (hMbS-hStrS) assembloids, hMbS and hStrS were generated separately, and later assembled by placing them in close proximity with each other in 1.5 ml microcentrifuge tubes for 3 days in an incubator. Media was carefully changed on day 2, and on the third day, assembloids were placed in 24-well or 60 mm ultralow attachment plates in the neural medium described above using a cut P1000 pipette tip. Assembly was performed at days 50-62 of hMbS and hStrS, and they were imaged at days 61 and 118 under environmentally controlled conditions using Leica TCS SP8 confocal microscope.

Example 2

Generation of Functional Human Striatum Spheroids (hStrS)

To generate hStrS resembling the Lateral Ganglionic Eminence (LGE) of the ventral forebrain, which ultimately give rise to the striatum, we dissociated hiPS cells enzymatically into a single cell suspension and aggregated them into spheroids using microwells (FIG. 1A). After dislodging the spheroids from the microwells, we treated them with dual SMAD inhibitors dorsomorphin and SB-431542 for 6 days followed by IWP-2 (day 7-23), Activin A (day 7-23) and Retinoid X receptor agonist SR11237 (day 12-23). This novel combination of patterning factors generated spheroids with high levels of the forebrain marker FOXG1 and LGE markers GSX2, MEIS2 and CTIP2, but not hypothalamus maker gene RAX and spinal cord marker gene HOXB4 at day 23 (FIG. 1B). At 80 days, hStrS showed the presence of $DARPP32^{+}GAD67^{+}$, $DARPP32^{+}CTIP2^{+}$, and $DARPP32^{+}/NeuN^{+}$ cells indicative of medium spiny neurons (FIG. 1C, D, E). To comprehensively characterize striatum lineage cells in hStrS, we dissociated single cells from day 80-83 hStrS by enzymatic dissociation and performed single cell-RNA-sequencing using 10× Genomics chromium system. We sequenced approximately 25,772 cells derived from hStrS, and clustering of all cells using the Uniform Manifold Approximation and Projection (UMAP) revealed that distinct populations of GABAergic neurons, neural progenitor cells, astrocytes, oligodendrocytes, and glutamatergic neurons (FIG. 1F). Furthermore, we mapped hStrS onto the BrainSpan human transcriptomic data set, and found that the GABAergic neuron cluster in hStrS showed the highest scaled correlation with striatum when compared to samples at PCW 20-25 (FIG. 1G). In hStrS, we detected strong expression of genes enriched in forebrain (FOXG 1) and LGE (DUO, DLX2, DLX5, DLX6, GSX2, ASCL1, FOXP1 and FOXP2), but not of genes in medial ganglionic eminence (NKX2-1) or in cerebral cortex (EMX1) (FIG. 1G). We further observed mDlx::eGFP cells that develop dendritic spine-like structures at 65 days in dissociated 2D culture in vitro (FIG. 1H), as well as day 120 of hStrS in 3D cultures (FIG. 11, J, K). To further examine if hStrS neurons shows electrophysiological features of striatal medium spiny neurons, we analyzed the intrinsic membrane properties of hStrS neurons. We found that 70% of hStrS cells at day 110-120 (12 out of 17 cells) showed inward rectification (FIG. 1M, N). At later stages of differentiation (day 160-170), we found that 15% of hStrS neurons (2 out of 13 cells) displayed slow-ramp depolarization with delayed first spike (FIG. 1O) and hyperpolarization of the resting membrane potential (−78.2±2.3 mV; FIG. 1P).

Example 3

Generation of Cortico-Striatal Assembloids (hCS-hStrS)

Figure 2:
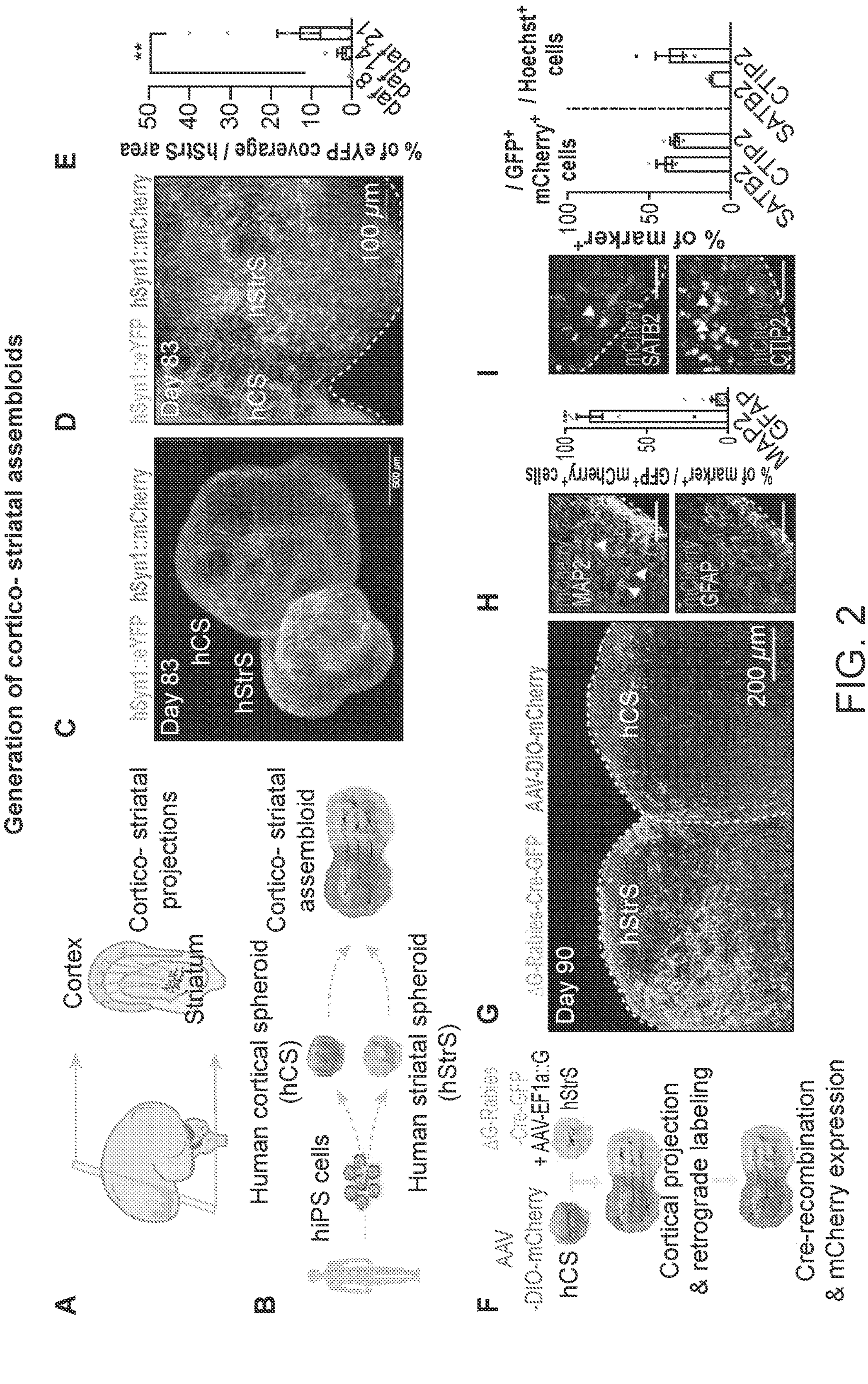
FIG. 2A-2R. Generation of cortico-striatal assembloids from human pluripotent stem cells (FIG. 2A,B) Scheme illustrating the cortico-striatal projections in the human developing brain, and in vitro modeling of cortico-striatal projection within cortico-striatal assembloids.
(FIG. 2C) Representative image showing the assembly of a fluorescently labeled hCS (AAV-DJ-hSyn::eYFP) and fluorescently labeled hStrS (AAV-DJ-hSyn::mCherry).
(FIG. 2D) Representative examples of cortico-striatal assembloids at 21 days after fusion.
(FIG. 2E) Quantification of the percentage eYFP coverage (indicating hCS originating axonal projections) in the hStrS area. n=6-8 assembloids. The images show that the spheroids form unidirectional projections, with neurons in the hCS projecting into the hStrS, but not vice versa.
(FIG. 2F) Retrograde viral tracing used to characterize hCS projections into the hStrS. hStrS were transfected with a ΔG-rabies virus carrying Cre-eGFP and with an AAV carrying the rabies glycoprotein (G). hCS were separately transfected with an AAV encoding mCherry under a double-floxed ORF (DIO-mCherry) before forming the cortico-striatal assembloids. Expression of mCherry indicates a neuron projecting from the hCS to the hStrS.
(FIG. 2G) Expression of GFP and mCherry was examined at 28 days after fusion.
(FIG. 2H,I) Quantification of proportion of projecting cells in hCS expressing neuronal marker MAPZ astrocyte marker GFAP, cortical projection neuron marker SATB2 or CTIP2. CTIP2$^{+}$ and SATB2$^{+}$ neurons were the main population of cells projecting from the hCS to hStrS in cortico-striatal assembloids.
(FIG. 2J) Optogenetics and live imaging used to test functionality of cortico-striatal assembloids. AAV-hSyn1::ChrimsonR was expressed in hCS and improved Cre (iCre) under a striatal mini-promotor gene GPR88 (AAV-Ple94::iCre) and DIO-GCaMP6s were expressed in the hStrS via AAVs and the assembloids assembled.
(FIG. 2K-M) Excitation of hCS neurons expressing ChrimsonR was able to elicit $Ca^{2+}$ activity in hStrS neurons, suggesting the formation of functional neural circuits in the assembloids.
(FIG. 2O) Schematic showing whole-cell patch-clamp recording in hStrS or cortico-striatal assembloids in slices.
(FIG. 2P) Representative electrophysiology traces of neurons in hStrS and hCS-hStrS neurons.
(FIG. 2Q) Frequency-current (F-I) curve showing spike frequency versus current injected in hStrS and hCS-hStrS neurons. n=17 cells in hStrS, n=25 cells in hCS-hStrS from 3 hiPS cell lines.
Figure 2:
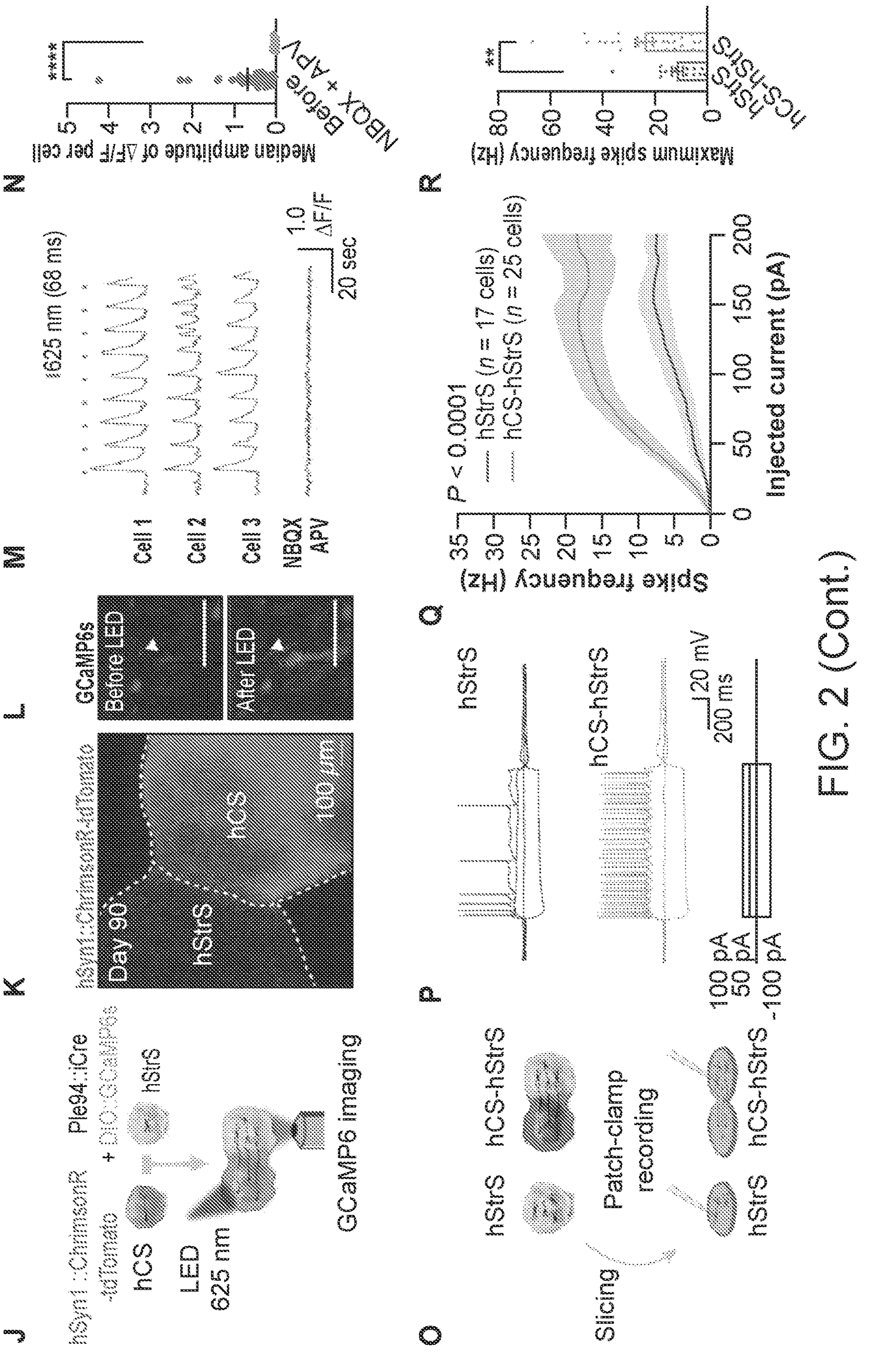

To develop a model forthe formation of cortico-striatal circuits in the developing human brain (FIG. 2A, B), hCS and hStrS that had been separately differentiated were placed adjacent to each other inside conical tube. After 3 days, the spheroids successfully assembled (FIG. 2C) and started forming cortico-striatal projections (FIG. 2D). The projections were unidirectional, with neurons in hCS projecting to hStrS, but not vice versa (FIG. 2D, E). To further characterize hCS projections into hStrS, we used retrograde viral tracing (FIG. 2F). We separately infected hStrS with a ΔG-rabies virus carrying Cre-eG FP and with an AAV carrying the rabies glycoprotein (G), and hCS with an AAV encoding mCherry under a double-floxed ORF (DIO-mCherry) (FIG. 2F). After virus infection, hCS and hStrS were assembled and expression of GFP and mCherry was examined at 28 days after fusion. We found that CTIP2* and $SATB2^{+}$ neurons, which are projecting from the cerebral cortex to the striatum in vivo, are main population of cells projecting from hCS to hStrS in cortico-striatal assembloids (FIG. 2H, I). To test the functionality of cortico-striatal assembloids, we coupled optogenetics and live imaging of $Ca^{2+}$ activity in neurons. Prior to assembly, hSyn1::ChrimsonR, which excite neurons in response to red-shifted light, was expressed in hCS, and improved Cre (iCre) under a striatal mini-promotor gene GPR88 (AAV-Ple94::iCre) and DIO-GCaMP6s for visualizing $Ca^{2+}$ activity of GABAergic neurons in the striatum, were expressed in hStrS via AAVs;

subsequently, these spheroids were assembled (FIG. 2J). Excitation of hCS neurons expressing ChrimsonR by 625 nm light was able to elicit $Ca^{2+}$ activity in hStrS neurons (FIG. 2K, L, M, N). To further examine whether the assembly of hCS and hStrS impact the electrophysiological properties of neurons in hStrS, we performed whole-cell patch clamp recordings in sliced cortico-striatal assembloids (FIG. 20). We found increased intrinsic excitability of hSyn1::eYFP labeled neurons on the hStrS side of hCS-hStrS as compared to neurons in hStrS at the same in vitro stage (FIG. 2P, Q, R). These results demonstrate the formation of functional neural circuits and maturation in cortico-striatal assembloids.

Example 4

Generation of Human Midbrain Spheroids (hMbS) and Midbrain-Striatal Assembloids (hMbS-hStrS)

Figure 3:
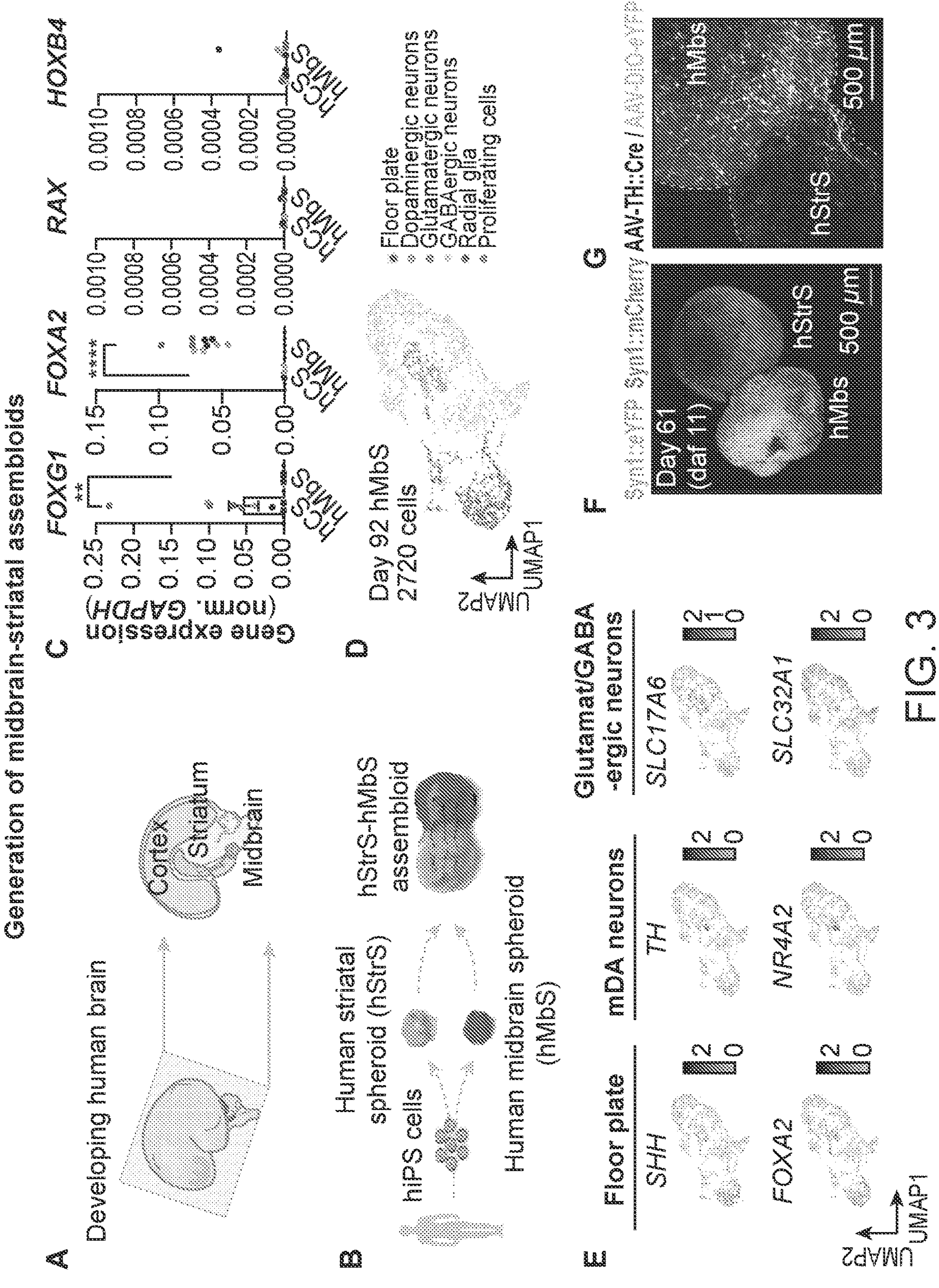
FIG. 3A-3G. Generation of midbrain-striatal assembloids from human pluripotent stem cells (FIG. 3A,B) Scheme illustrating the dopaminergic inputs from midbrain to striatum, and in vitro modeling of midbrain-striatal pathway with midbrain-striatal assembloids (FIG. 3C) hMbS at day 23 of culture show low levels of the forebrain marker FOXG1, and high levels of the floor plate mesencephalic dopaminergic neurons marker FOXA2 without expression of hypothalamus marker RAX and spinal cord marker HOXB4.

Dopaminergic inputs from midbrain to the striatum plays a crucial role in the development and maturation of striatum (Kozorovitskiy et al., 2015). Moreover, GABAergic modulation of the midbrain from the striatum is an essential component of the basal ganglia direct pathway. To further model of this complex circuit, we derived hMbS from iPS cells, and assembled with hStrS (FIG. 3A, B). hMbS at day 23 of culture showed low levels of the forebrain marker FOXG1, and high levels of floor plate mesencephalic dopaminergic neurons marker FOXA2, but not hypothalamus maker gene RAX and spinal cord marker gene HOXB4 (FIG. 3C). To comprehensively characterize striatum lineage cells in hMbS, we dissociated single cells from day 92 hMbS and performed single cell-RNA-sequencing using 10× Genomics chromium system. We sequenced approximately 2,720 cells. Clustering of all cells using the UMAP revealed that distinct populations of midbrain dopaminergic neurons, floor plate, neural progenitor cells, glutamatergic neurons, and GABAergic neurons (FIG. 3D, E). To generate midbrain-striatal assembloids, hMbS labeled with Syn1::eYFP, and hStrS labeled with Syn1::m Cherry were placed adjucent to each other inside conical tube. After 3 days, these spheroids were assembled (FIG. 3F). In addition, hMbS co-infected with AAV-rTH::Cre and AAV-DIO-eYFP and hStrS were assembled and started formation of projections from dopaminergic neurons in hMbS to hStrS (FIG. 3G). This preparation can now be used in combination with hCS to concomitantly study glutamatergic and dopaminergic input into the striatum, which has broad applications.

This is the first 3D human model of the cortico-striatal and striato-midbrain circuits generated by in vitro assembly from human pluripotent stem cells. A number of applications can use this system, including developing advanced disease models (Huntington disease, Parkinson's disease, Phelan McDermid and other forms of ASD, etc.), developing models of axon degeneration, screening small molecules to rescue disease specific phenotypes, testing gene therapy applications.

REFERENCES

Shepherd, Gordon M. G. "Corticostriatal Connectivity and Its Role in Disease." *Nature Reviews Neuroscience* 14, no. 4 {2013): 278-91.

Pasca. Sergiu P. "The Rise of Three-Dimensional Human Brain Cultures." *Nature PublishingGroup* 553, no. 7689 {2018): 437-45.

Birey, Fikri, Jimena Andersen, Christopher D. Makinson, Saiful Islam, Wu Wei, Nina Huber, H. Christina Fan, et al. "Assembly of Functionally Integrated Human Forebrain Spheroids." Nature 545, no. 7652 {2017): 54-59.

Yager L M, Garcia A F, Wunsch A M, Ferguson S M. "The ins and outs of the striatum: role in drug addiction." Neuroscience. 2015.

Yoon, Se-Jin, Lubayna S Elahi, Anca M Pasca, Rebecca M Marton, Aaron Gordon, Omer Revah, Yuki Miura, et al. "Reliability of Human Cortical Organoid Generation." *Nature Methods,* 2018.

Kozorovitskiy, Yevgenia, Rui Peixoto, Wengang Wang, Arpiar Saunders, and Bernardo L Sabatini. "Neuromodulation of Excitatory Synaptogenesis in Striatal Development." *ELife* 4 {2015): 1-18.

That which is claimed is:

1. A method for producing a midbrain-striatal assembloid in vitro, the method comprising:

(i)(a) inducing a human pluripotent stem cell in a suspension culture to a neural fate in a medium to provide a neural spheroid, wherein the medium comprises two SMAD pathway inhibitors selected from the group of dorsomorphin, LDN-193189, LY364947 and SB-431542, a fibroblast growth factor (FGF), and a sonic hedgehog pathway agonist, wherein the sonic hedgehog pathway agonist is smoothened agonist (SAG);

(i)(b) differentiating the neural spheroid into a midbrain spheroid (hMbS) in a neural medium supplemented with FGF8, SAG, an inhibitor of BMP, and an inhibitor of GSK-3, (ii)(a) inducing a human pluripotent stem cell in suspension culture to a neural fate in a medium to provide a neural spheroid, wherein the medium comprises two SMAD pathway inhibitors selected from the group of dorsomorphin, LDN-193189, LY364947 and SB-431542, optionally further comprising an inhibitor of the Wnt pathway, (ii)(b) differentiating the neural spheroid into a human striatal spheroid (hStrS) in suspension culture in a neural medium comprising an inhibitor of the Wnt pathway, an activin A, and a retinoid X receptor (RXR) agonist; and (iii) culturing the hStrS and hMbS in direct contact in neural medium, such that the midbrain-striatal assembloid comprises human midbrain neurons projecting from the hMbS into the hStrS.

2. The method of claim 1, wherein, in step (i)(a), culturing in the medium comprising the SMAD pathway inhibitors is for a period of from 4 to 10 days, adding the FGF8 and SAG to the medium after about 3 days of culture, wherein the FGF8 and SAG are maintained for a period of about 1 day, and optionally wherein the FGF8 and SAG and are maintained for a period of about 1 day.

3. The method of claim 1, wherein differentiating the neural spheroid into the hMbS in step (i)(b) further comprises culturing the neural spheroid in suspension culture in additional neural medium supplemented with brain-derived neurotrophic factor (BDNF), NT3, L-Ascorbic Acid, CAMP, DHA, and DAPT, optionally wherein , the inhibitor of BMP is LND 193189 and the inhibitor of GSK-3 is CHIR99021.

4. The method of claim 1, wherein the hStrS and hMbS are cultured in direct contact for at least 10 days, and optionally wherein the suspension culture is feeder layer free.

5. A midbrain-striatal assembloid produced by the method of claim 1.

* * * * *